United States Patent
Li et al.

(10) Patent No.: US 12,282,013 B2
(45) Date of Patent: Apr. 22, 2025

(54) EX VIVO METHODS OF SCREENING FOR, AND CHARACTERIZING, CARDIAC THERAPEUTICS USING PRELOADED CARDIAC TISSUES

(71) Applicant: NOVOHEART INTERNATIONAL LIMITED, Kowloon (HK)

(72) Inventors: Ronald A. Li, Hong Kong (CN); Kevin D. Costa, New York, NY (US)

(73) Assignee: NOVOHEART INTERNATIONAL LIMITED, Kowloon (HK)

( * ) Notice: Subject to any disclaimer, the term of this patent is extended or adjusted under 35 U.S.C. 154(b) by 303 days.

(21) Appl. No.: 17/254,264

(22) PCT Filed: Jun. 18, 2019

(86) PCT No.: PCT/IB2019/055118
§ 371 (c)(1),
(2) Date: Dec. 19, 2020

(87) PCT Pub. No.: WO2019/044044
PCT Pub. Date: Dec. 26, 2019

(65) Prior Publication Data
US 2021/0263010 A1 Aug. 26, 2021

Related U.S. Application Data

(60) Provisional application No. 62/687,706, filed on Jun. 20, 2018.

(51) Int. Cl.
*B01L 7/00* (2006.01)
*B01F 33/302* (2022.01)
(Continued)

(52) U.S. Cl.
CPC .................. *G01N 33/4833* (2013.01)

(58) Field of Classification Search
CPC .............. G01N 33/4833; C12N 5/0657; C12N 2502/1323; C12N 2502/1329;
(Continued)

(56) References Cited

U.S. PATENT DOCUMENTS

2007/0238169 A1* 10/2007 Abilez .................. C12M 25/14
435/308.1
2014/0342394 A1 11/2014 Parker et al.
(Continued)

FOREIGN PATENT DOCUMENTS

JP 3692147 B2 * 9/2005 ............. A61F 2/022
WO 2018/027105 A1 2/2018

OTHER PUBLICATIONS

Al-Mahdawi et al., Gaa repeat expansion mutation mouse models of Friedreich ataxia exhibit oxidative stress leading to progressive neuronal and cardiac pathology, Genomics, 88:580-590 (2006).
(Continued)

*Primary Examiner* — Jennifer Wecker
*Assistant Examiner* — Oyeleye Alexander Alabi
(74) *Attorney, Agent, or Firm* — MARSHALL, GERSTEIN & BORUN LLP

(57) ABSTRACT

Provided are methods and materials for assaying known and candidate therapeutics for inotropic cardiac effects in one or more in vitro assay formats comprising preloaded cardiac tissues and/or organoids.

22 Claims, 19 Drawing Sheets

(51) Int. Cl.
  *B01F 33/3033* (2022.01)
  *C12Q 1/6848* (2018.01)
  *C12Q 1/686* (2018.01)
  *G01N 33/483* (2006.01)

(58) Field of Classification Search
  CPC ............ C12N 2506/02; C12N 2513/00; C12N 2527/00; C12N 2529/00; C12N 2533/54; C12N 2533/76
  See application file for complete search history.

(56) References Cited

U.S. PATENT DOCUMENTS

| | | | |
|---|---|---|---|
| 2016/0363600 A1* | 12/2016 | Sniadecki | ......... B01L 3/502715 |
| 2017/0002330 A1 | 1/2017 | Vunjak-Novakovic et al. | |
| 2018/0209957 A1* | 7/2018 | Parker | ................ G01N 33/5008 |
| 2018/0291350 A1* | 10/2018 | Murphy | ............... C12N 5/0697 |

OTHER PUBLICATIONS

Casazza et al., The varying evolution of Friedreich's ataxia cardiomyopathy, Am. J. Cardiol., 77:895-898 (1996).
Cashman et al., Construction of defined human engineered cardiac tissues to study mechanisms of cardiac cell therapy, J. Vis. Exp., 109:e53447 (2016).
Chan et al., Label-free separation of human embryonic stem cells and their cardiac derivatives using Raman spectroscopy, Anal. Cham., 81:1324-1331 (2009).
Chen et al., Phospholamban as a Crucial Determinant of the Inotropic Response of Human Pluripotent Stem Cell-Derived Ventricular Cardiomyocytes and Engineered 3-Dimensional Tissue Constructs, Circ. Arrthyhm. Electrophysiol., 8:193-201 (2015).
Chen et al., Shrink-film configurable multiscale wrinkles for functional alignment of human embryonic stem cells and their cardiac derivatives, Adv. Mater., 23:5785-5791 (2011).
Chow et al., Epigenetic regulation of the electrophysiological phenotype of human embryonic stem cell-derived ventricular cardiomyocytes: insights for driven maturation and hypertrophic growth, Stem Cells Dev., 22:2678-2690 (2013).
Dixon et al., The role of iron and reactive oxygen species in cell death, Nat. Chem. Biol., 10:9-17 (2014).
Durr et al., Clinical and genetic abnormalities in patients with Friedreich's ataxia, N. Engl. J. Med., 335:1169-1175 (1996).
Edenharter et al., Overexpression of Drosophila frataxin triggers cell death in an iron-dependent manner, J. Neurogenet., 31:189-202 (2017).
Efraim, Y., et al., Biohybrid cardiac ECM-based hydrogels improve long term cardiac function post myocardial infarction, Acta Biomaterialia, 50:220-233 (2016).
European Application No. 19822894.2, European Search Report and Opinion, mailed Feb. 23, 2022.
European Application No. 19822894.2, European Search Report and Opinion, mailed Jun. 1, 2022.
Filla et al., The relationship between trinucleotide (gaa) repeat length and clinical features in Friedreich ataxia, Am. J. Hum. Genet., 59:554-560 (1996).
Fu et al., Distinct roles of microRNA-1 and-499 in ventlicular specification and functional maturation of human embryonic stem cell-derived cardiomyocytes, PLoS One, 6:e27417 (2011).
Fu et al., Na+/Ca2+ exchanger is a determinant of excitation-contraction coupling in human embryonic stem cell-derived ventricular cardiomyocytes, Stem Cells Dev., 19:773-782 (2010).
Goffart et al., Regulation of mitochondrial proliferation in the heart: Power-plant failure contributes to cardiac failure in hypertrophy, Cardiovasc Res., 64(2):198-207 (2004).
Hick et al., Neurons and cardiomyocytes derived from induced pluripotent stem cells as a model for mitochondrial defects in Friedreich's ataxia, Dis. Model Mech., 6:608-621 (2013).
International Application No. PCT/IB19/55118, International Preliminary Report on Patentability, mailed Dec. 30, 2020.
International Application No. PCT/IB19/55118, International Search Report and Written Opinion, mailed Nov. 27, 2019.
Isnard et al., Correlation between left ventricular hypertrophy and gaa trinucleotide repeat length in Friedreich's ataxia, Circulation, 95:2247-2249 (1997).
Karakikes et al., Correction of human phospholamban RI4del mutation associated with cardiomyopathy using targeted nucleases and combination therapy, Nat. Commun., 6:6955 (2015).
Karakikes et al., Small Molecule-Mediated Directed Differentiation of Human Embryonic Stem Cells Toward Ventricular Cardiomyocytes, Stem Cells Transl. Med., 3:18-31 (2014).
Keung et al., Non-cell autonomous cues for enhanced functionality of human embryonic stem cell-derived cardiomyocytes via maturation of sarcolemmal and mitochondrial KATP channels, Sci. Rep., 6:34154 (2016).
Kipps et al., The longitudinal course of cardiomyopathy in Friedreich's ataxia during childhood, Pediatr Cardiol., 30:306-310 (2009).
Lee et al., Efficient attenuation of Friedreich's ataxia (FRDA) cardiomyopathy by modulation of iron homeostasis-human induced pluripotent stem cell (hiPSC) as a drug screening platform for FRDA, Int. J. Cardiol., 203:964-971 (2016).
Lee et al., Modeling of Friedreich ataxia-related iron overloading cardiomyopathy using patient-specific-induced pluripotent stem cells, Pflugers Arch., 466:1831-1844 (2014).
Lee, S., et al., A strain-absorbing design for tissue-machine interfaces using a tunable adhesive gel., Nature Communication, 5:1-8 ID No. 5898, (2014).
Li et al., Bioengineering an electro-mechanically functional miniature ventricular heart chamber from human pluripotent stem cells, Biomaterials, 163:116-127 (2018).
Li et al., Mechanistic basis of excitation-contraction coupling in human pluripotent stem cell-derived ventricular cardiomyocytes revealed by Ca2+ spark characteristics: Direct evidence of functional Ca2+-induced Ca2+ release, Heart Rhythm, 11:133-140 (2014).
Lieu et al., Absence of Transverse Tubules Contributes to Non-Uniform Ca2+ Wavefronts in Mouse and Human Embryonic Stem Cell-Derived Cardiomyocytes, Stem Cells Dev., 18:1493-1500 (2009).
Lieu et al., Mechanism-Based Facilitated Maturation of Human Pluripotent Stem Cell-Derived Cardiomyocytes, Circ. Arrhythm. Electrophysiol., 6:191-201 (2013).
Liu et al., Facilitated maturation of Ca2+ handling properties of human embryonic stem cell-derived cardiomyocytes by calsequestrin expression, Am. J. Physiol. Cell Physiol., 297:C152-159 (2009).
Liu et al., Functional sarcoplasmic reticulum for calcium handling of human embryonic stem cell-derived cardiomyocytes: insights for driven maturation, Stem Cells., 12:3038-44 (2007).
Liu, X. H., et al., Biomimetic scaffolds enhancing cardiomyocyte growth and cardiac tissue development, Chinese Master's Theses Full-text Database Medicine and Health Sciences, E080-14: 36-57 (2016).
Lopaschuk et al., Energy metabolic phenotype of the cardiomyocyte during development, differentiation, and postnatal maturation, J. Cardiovasc Pharmacol., 56:130-140 (2010).
Luna et al., Multiscale Biomimetic Topography for the Alignment of Neonatal and Embryonic Stem Cell-Derived Heart Cells, Tissue Eng Part C Methods, 17:579-588 (2011).
Lynch et al., Management and therapy for cardiomyopathy in Friedreich's ataxia, Expert Rev Cardiovasc Ther., 10:767-777 (2012).
Martelli et al., Dysregulation of cellular iron metabolism in Friedreich ataxia: From primary iron-sulfur cluster deficit to mitochondrial iron accumulation, Front. Pharmacol., 5:130 (2014).
Miranda et al., Frataxin knockin mouse, FEBS Lett., 512:291-297 (2002).
Ohya, T., et al., Simple action potential measurement of cardiac cell sheet utilizing electronic sheet, Artificial Life and Robotics., 23:321-327 (2018).
Payne et al., Cardiomyopathy of Friedreich's ataxia: Use of mouse models to understand human disease and guide therapeutic development, Pediatr Cardiol., 32:366-378 (2011).
Poon et al., Proteomic Analysis of Human Pluripotent Stem Cell-Derived, Fetal, and Adult Ventricular Cardiomyocytes Reveals

(56) References Cited

OTHER PUBLICATIONS

Pathways Crucial for Cardiac Metabolism and Maturation, Circ. Cardiovasc Genet., 8:427-436 (2015).
Poon et al., Transcriptome-Guided Functional Analyses Reveal Novel Biological Properties and Regulatory Hierarchy of Human Embryonic Stem Cell-Derived Ventricular Cardiomyocytes Crucial for Maturation, PLoS One, 8:e77784 (2013).
Puccio et al., Mouse models for Friedreich ataxia exhibit cardiomyopathy, sensory nerve defect and fe—s enzyme deficiency followed by intramitochondrial iron deposits, Nat. Genet., 27:181-186 (2001).
Rajagopalan et al., Analysis of the factors influencing the cardiac phenotype in Friedreich's ataxia, Mov. Disord., 25:846-852 (2010).
Ramirez et al., Pathology of intercalated discs in Friedreich cardiomyopathy, J. Am. Coll. Cardiol., 66:1739-1740 (2015).
Roquemore, E., et al., Cell-based early d rug safety testing, Euro Biotech News., 9(11-12):34-40 (2010).
Shum et al., A micropatterned human pluripotent stem cell-based ventricular cardiac anisotropic sheet for visualizing drug-induced arrhythmogenicity, Adv. Mater., 29(1):1602448 (2017).
Takamatsu, S., et al., Direct patterning of organic conductors on knitted textiles for long-electrocardiogra Scientific Report, 5:1-7 (2015).
Tang, T., et al., Theoretical model and numerical simulation of cardiac myocyte reorientation during cyclic substrate stretch, J. Tsing hua Univ. ( Sci. & Tech.)., 50:(5):660-664 (2010).
Tsou et al., Mortality in Friedreich ataxia, J. Neural. Sci., 307:46-49 (2011).
Turnbull et al., Advancing functional engineered cardiac tissues toward a preclinical model of human myocardium, FASEB J., 28:644-654 (2014).
Wang et al., Effect of engineered anisotropy on the susceptibility of human pluripotent stem cell-derived ventricular cardiomyocytes to arrhythmias, Biomaterials, 34:8878-8886 (2013).
Wang et al., Electrophysiological properties of pluripotent human and mouse embryonic stem cells, Stem Cells, 23(10):1526-34 (2005).
Weidemann et al., The cardiomyopathy in Friedreich's ataxia—new biomarker for staging cardiac involvement, Int. J. Cardiol., 194:50-57 (2015).
Weng et al., A Simple, Cost-Effective but Highly Efficient System for Deriving Ventricular Cardiomyocytes from Human Pluripotent Stem Cells, Stem Cells Dev., 23:1704-1716 (2014).
Wilson et al., Dynamic microRNA expression programs during cardiac differentiation of human embryonic stem cells: role for miR-499, Circ. Cardiovasc Genet., 3:426-435 (2010).
Ye, G., et al., Conductive biomaterials in cardiac tissue engineering, Biotarget., 2(9):1-7 (2017).
Zhang et al., Consensus Comparative Analysis of Human Embryonic Stem Cell-Derived Cardiomyocytes, PLoS One, 10:e0125442 (2015).

* cited by examiner

Figure 11

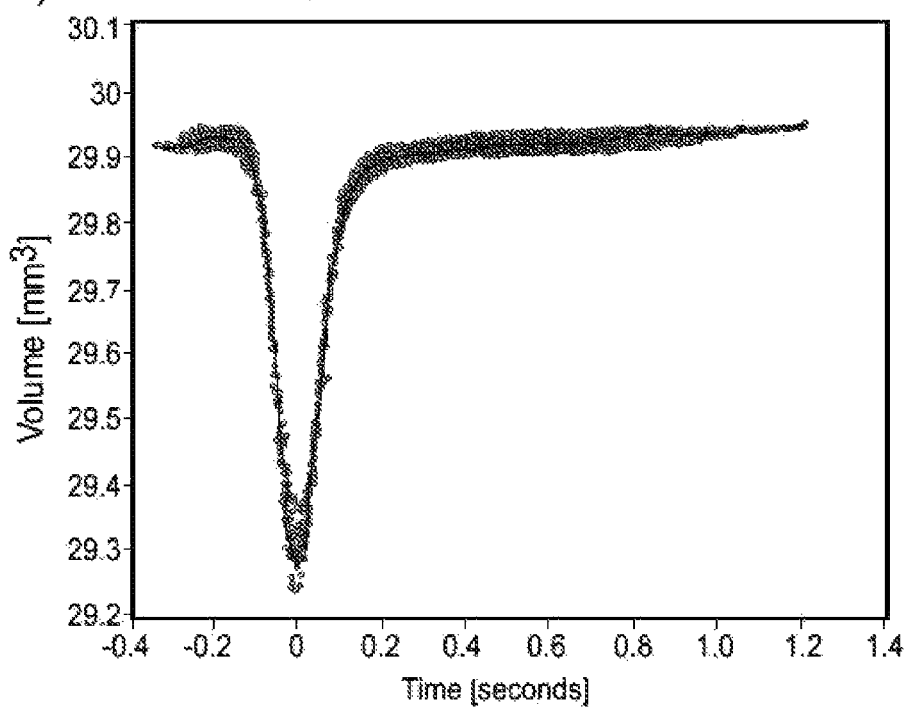
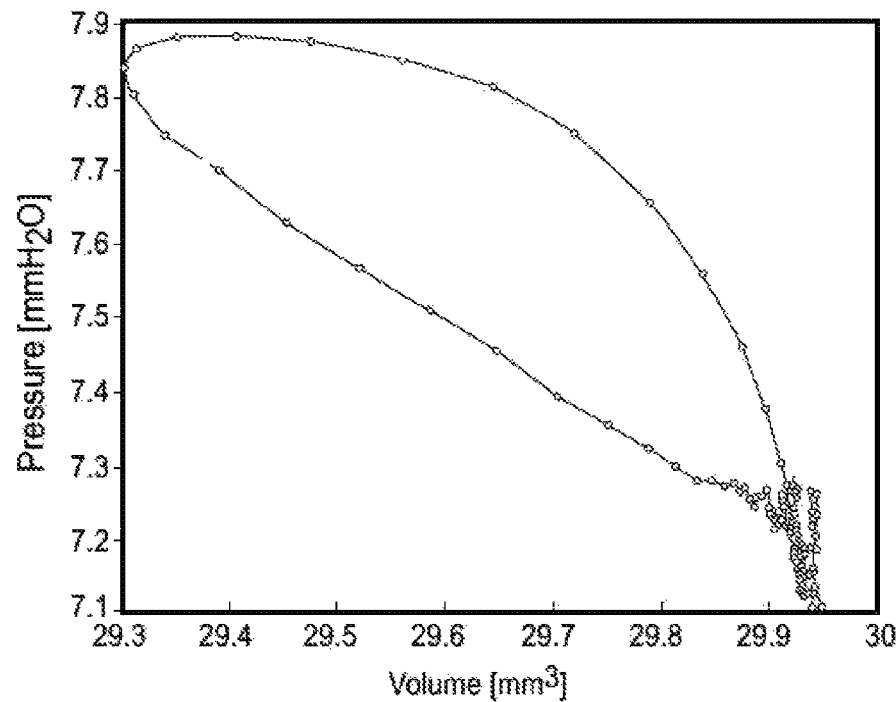
Figure 15

EX VIVO METHODS OF SCREENING FOR, AND CHARACTERIZING, CARDIAC THERAPEUTICS USING PRELOADED CARDIAC TISSUES

CROSS-REFERENCE TO RELATED APPLICATIONS

This application claims the priority benefit under 35 U.S.C. § 119(e) of U.S. Provisional Patent Application No. 62/687,706, filed Jun. 20, 2018, the disclosure of which is incorporated herein by reference in its entirety.

FIELD

The disclosed materials and methods relate generally to the field of medicine and the assessment of known or candidate therapeutics, and more particularly to the field of cardiophysiology.

BACKGROUND

Cardiac drug discovery and development continue to be inefficient and expensive processes, with cardiotoxicity being the leading cause for attrition. Although traditional animal models are available, major species differences limit their ability to predict pharmacological responses in humans. As such, various engineered tissue models based on human pluripotent stem cell-derived cardiomyocytes have been developed for studying contractility in the context of genuine human heart cells. Though these tissue models are state-of-the-art, significant variability is often observed. This signal-to-noise issue is particularly problematic where phenotypes or responses are not as extreme as those often seen in patients with monogenic diseases. Indeed, weak or null responses to positive inotropic agents are often reported with engineered heart tissues. A review of the literature indicates that the studies of engineered human cardiac tissue function have been performed with non-physiological passive stretch, implying low resting sarcomere lengths with fewer actin and myosin cross bridges. This risks underestimating or misinterpreting the bona fide physiological responses in the heart, which functions by default in a stretched state. For example, inotropic responses of cardiac contractility to pharmacological compounds observed under passive stretch, and the potency observed based on the dose-response relationship, may not necessarily reflect that observed in the native heart in the presence of a preload. Diseases that afflict the heart might also be inaccurately modeled in unstretched tissues, with phenotypes underestimated relative to those observed clinically.

Much effort has been expended to advance our understanding of the human cardiovascular system and human cardiac care, but a need continues to exist in the art for biological models that can rapidly and accurately reveal the pharmacological effects of known or candidate therapeutics, including cardiac therapeutics, and/or can rapidly and accurately reveal the cardiac effects in cells from patients having diseases that are conventionally understood as being non-cardiac in nature.

SUMMARY

Based on the understanding that the activation of sarcomeric contraction is length-dependent, an expectation was developed that an optimal range of preloads is needed for improving the signal-to-noise ratios (i.e., lowering result variability) and therefore, the sensitivity of engineered cardiac tissues and chambers for detecting phenotypic differences in contractility. The sensitivities of human ventricular cardiac tissue strips (hvCTS) and organoid chambers (hvCOC) were initially examined for a series of pharmacological agents with inotropic effects. The hvCTS showed detectable, although more modest, responses to positive inotropes compared to the more prominent effects observed with hvCOC (see, e.g., FIG. 6). As the preload increased, the force of hvCTS and the pressure-volume loop area of hvCOC increased accordingly until a plateau was reached. As for pharmacological responses, statistically insignificant differences measured during passive stretch became significant when the optimal tissue length $L_{max}$ was approached. In other cases, the standard deviations became smaller with tighter data sets. Similarly, undetectable phenotypic differences in the contractility of induced pluripotent stem cell-based (i.e., iPSC-based) disease models became significant with isometric measurements at controlled tissue lengths. Thus, physiological preloads are critical for revealing positive inotropy and contractile phenotypes using human pluripotent stem cell-derived engineered cardiac tissues and chambers.

The investigations disclosed herein led to the development of in vitro cardiac assay formats based on cardiac tissue strips (CTS) or cardiac organoid chambers (COC). The cardiac tissue strips suitable for the assays disclosed herein include, but are not limited to, human cardiac tissue strips, such as human ventricular cardiac tissue strips (hvCTS), e.g., human pluripotent stem cell-derived ventricular cardiac tissue strips. The cardiac organoid chambers, each comprising a human cardiac organoid, include, but are not limited to, human cardiac organoid chambers, such as human ventricular cardiac organoid chambers (hvCOC), e.g., human pluripotent stem cell-derived ventricular cardiac organoid chambers.

The assay formats of the disclosure more closely mirror the in vivo conditions of the beating heart and, thus, provide a truer measure of the cardiac effects of tested therapeutics, whether known or candidate therapeutics, and whether cardiac or non-cardiac therapeutics exhibiting at least one cardiac effect. The data disclosed herein establish that the assay formats also provide sensitive, accurate, and reproducible results to efficiently guide clinicians in the selection and optimization of therapeutics for treating a variety of diseases, including cardiac diseases. The assay formats universally exploit the preloading of cardiac tissues and/or organoids to more closely reflect in vivo conditions where cardiomyocytes are preloaded, or under tension in the non-contracting or resting state. The preloading of cardiac tissues and/or organoids results in an apparent augmentation of the inotropic response of the cardiac tissue/organoids to the known or candidate therapeutics under test by unmasking the full extent of an inotropic response, which may be a positive or negative inotropic response. The preloading of cardiac tissues/organoids in the assay formats also improves the sensitivity of the assays to electrophysiological responses to the known or candidate therapeutics being assessed.

Beyond assessing the cardiac effects of known or candidate therapeutics, the disclosure also provides comparative assays for measuring the differences between healthy and diseased cardiac tissues and/or organs. Each of the preloaded assay formats disclosed herein is useful in comparative assays of healthy and diseased tissues/organoids. In providing a truer picture of the cardiac effects of known or candidate therapeutics, the disclosed assay formats also yield amplified phenotypic differences between healthy and diseased tissues/organoids that more accurately reflect their phenotypic difference(s).

In accordance with the foregoing observations, one aspect of the disclosure is drawn to a method of assessing the effect of a compound on a cardiomyocyte comprising: (a) preloading cardiomyocytes of a biocompatible gel apparatus by moving a biocompatible gel support member not fixed in space to stretch the biocompatible gel comprising cardiomyocytes, wherein the biocompatible gel apparatus comprises: (i) a biocompatible gel comprising a plurality of cardiomyocytes; (ii) a biocompatible support apparatus for suspending the biocompatible gel, wherein the biocompatible support apparatus comprises at least two support members, wherein a subset of the support members is fixed in space, and wherein the biocompatible gel and biocompatible support apparatus form a cardiac tissue strip comprising cardiomyocytes; (iii) a motor attached to at least one support member that is not fixed in space for stretching the biocompatible gel in at least one dimension; (iv) a detection device for detecting movement of the biocompatible gel; and (v) an electrical power source for applying an electrical pacing stimulus to the biocompatible gel; (b) administering an effective amount of a compound to the biocompatible gel; and (c) measuring the response of the biocompatible gel comprising cardiomyocytes to the compound. In some embodiments, the response being measured is a positive inotropic response or a negative inotropic response. In some embodiments, the compound is a pharmacological agent and the response being measured is a response to the pharmacological agent.

Embodiments are contemplated in which the compound is a known therapeutic, such as methods wherein the known therapeutic is useful in treating a cardiac disease or disorder, including but not limited to, dilated cardiomyopathy, hypertrophic cardiomyopathy, pulmonary atresia, Tetralogy of Fallot, dilated cardiomyopathy with ataxia or heterotaxy syndrome. In some embodiments, the known therapeutic is useful in treating a non-cardiac disease or disorder, such as Friedreich's ataxia (FRDA), Kearns-Sayre syndrome, carbohydrate-deficient glycoprotein syndrome type Ia (phosphomannomutase-2 congenital defect of glycosylation Ia or PMM2-CDG-Ia), spinocerebellar ataxia, Wilson disease, Dandy-Walker syndrome, Leigh disease, mitochondrial encephalomyopathy, lactic acidosis, and stroke-like episodes (MELAS), or myoclonic epilepsy with ragged red fibers (MERRF).

In some embodiments, the compound is a candidate therapeutic for a cardiac disease or disorder, or for a non-cardiac disease or disorder. Exemplary methods according to this aspect of the disclosure include methods wherein the motor induces a change in length of the hydrogel comprising cardiomyocytes of between 1-50%, for example 20-30%, of the length of the preloaded hydrogel comprising cardiomyocytes prior to administration of the compound.

In some embodiments, the cardiomyocyte is a healthy cardiomyocyte, the method further comprising a comparison of the effect of the compound on the healthy cardiomyocyte to the effect of the compound on a diseased cardiomyocyte to reveal at least one phenotypic difference between the healthy and diseased cardiomyocytes. In some embodiments, the healthy cardiomyocytes and the diseased cardiomyocytes are subjected to the same degree of physiomimetic stretch. Embodiments of this aspect of the disclosure include methods wherein the phenotypic difference is a difference in contractile force, contractile rate, or relaxation rate, such as methods wherein the diseased cardiomyocytes exhibit a contractile force of less than 20 µN. The methods of this aspect include methods wherein the diseased cardiomyocytes are from a subject with Friedrich's Ataxia. In some embodiments, the phenotypic difference increases as the degree of stretching increases up to the optimum muscle length for force production ($L_{max}$). In some embodiments, the phenotypic difference is determined at 50% $L_{max}$. In some embodiments, the phenotypic difference for contractile force is determined at 80-100% $L_{max}$. In some embodiments, the phenotypic difference for contractile rate is determined at 80-100% $L_{max}$. In some embodiments, the phenotypic difference for relaxation rate is determined at 90-100% $L_{max}$.

Another aspect according to the disclosure is a method for assaying a response of a cardiac organoid to a compound comprising: (a) preloading a cardiac organoid by adjusting the hydrostatic pressure to expand the cardiac organoid, wherein the cardiac organoid is housed in at least one organoid module comprising: (i) at least one organoid module, wherein each organoid module comprises a media inlet, a media outlet, and at least one wall compatible with an external detection device, wherein the cardiac organoid comprises at least one human cell, wherein the cell is a human embryonic stem cell, a human adult stem cell, a human induced pluripotent stem cell, a cell derived from a human tissue, or a progenitor cell of a human tissue, and wherein the cardiac organoid is in fluid communication with a fluid pump or a fluid reservoir comprising an adjustable volume of fluid, wherein the fluid pump or fluid reservoir modulates the pressure within the organoid; (ii) a mirror arrangement for simultaneous monitoring of any biological development of the cardiac organoid in each of at least two organoid modules; and (iii) a detection device for observing the monitored biological development of the cardiac organoid in each of at least two organoid modules; (b) administering the compound to the cardiac organoid; and (c) detecting a response of the cardiac organoid to the compound.

In some embodiments of this aspect of the disclosure, the response is a positive inotropic response or a negative inotropic response. In some embodiments, the compound is a pharmacological agent and the response is a response to the pharmacological agent. In some embodiments, the compound is a known therapeutic. In some embodiments, the known therapeutic is useful in treating a cardiac disease or disorder. In some embodiments, the cardiac disease or disorder is dilated cardiomyopathy, hypertrophic cardiomyopathy, pulmonary atresia, Tetralogy of Fallot, dilated cardiomyopathy with ataxia or heterotaxy syndrome. In some embodiments, the known therapeutic is useful in treating a non-cardiac disease or disorder having at least one cardiac effect. In some embodiments, the non-cardiac disease or disorder is Friedreich's ataxia (FRDA), Kearns-Sayre syndrome, carbohydrate-deficient glycoprotein syndrome type Ia (phosphomannomutase-2 congenital defect of glycosylation Ia or PMM2-CDG-Ia), spinocerebellar ataxia, Wilson disease, Dandy-Walker syndrome, Leigh disease, mitochondrial encephalomyopathy, lactic acidosis, and stroke-like episodes (MELAS), myoclonic epilepsy with ragged red fibers (MERRF) or heterotaxy syndrome. In some embodiments, the compound is a candidate therapeutic for a cardiac disease or disorder, or for a non-cardiac disease or disorder. In some embodiments, the pressure inside the organoid chamber induces a change in stroke work of between 1-50% of stroke work of the preloaded organoid chamber comprising cardiomyocytes prior to administration of the compound. In some embodiments, the change in stroke work is between 20-30% of the preloaded organoid chamber comprising cardiomyocytes prior to administration of the compound.

In some embodiments according to this aspect of the disclosure, the cardiac organoid is a healthy cardiac organoid, the method further comprising a comparison of the effect of the compound on the healthy cardiac organoid to the effect of the compound on a diseased cardiac organoid to reveal at least one phenotypic difference between the healthy and diseased cardiac organoids. In some embodiments, the pressure applied to the healthy cardiac organoid and the diseased cardiac organoid is the same. In some embodiments, the phenotypic difference is a difference in contractile force, contractile rate, or relaxation rate. In some embodiments, the diseased cardiac organoid exhibits a developed pressure of less than 2 mm $H_2O$. In some embodiments, the diseased cardiac organoid is from a subject with Friedrich's Ataxia. In some embodiments, the cardiac organoid is electrically paced using 5 volts/cm at a frequency of 1.5 Hz. In some embodiments, the stroke work is greater in the presence of the compound than in its absence, at a positive preloading of the cardiac organoid of at least 2.5 mm $H_2O$. In some embodiments, the difference in stroke work increases as the degree of preloading increases from 2.5 mm $H_2O$ to 7.5 mm $H_2O$. In some embodiments, the stroke work is lower in the presence of the compound than in its absence at a positive preloading of the cardiac organoid of at least 2.5 mm $H_2O$. In some embodiments, the difference in stroke work increases as the degree of preloading increases from 2.5 mm $H_2O$ to 7.5 mm $H_2O$.

Other features and advantages of the disclosed subject matter will be apparent from the following detailed description and figures, and from the claims.

BRIEF DESCRIPTION OF THE DRAWINGS

FIG. 2A) The human ventricular cardiac tissue strip (hvCTS) assay detected a trend of increasing contractile force when paced at 1 Hz and treated with increasing concentrations of the positive inotropes isoproterenol (left) and levosimendan (right), but they exhibit blunted responses when measured in their unstretched states. FIG. 2B) The human ventricular cardiac organoid chamber (hvCOC) assay shows an increase in area in the pressure-volume loops after treating with positive inotropes isoproterenol (left) and levosimendan (right), in the absence of preload. FIG. 2C) The hvCOC assay has an enhanced sensitivity to positive inotropes isoproterenol (left) and levosimendan (right) compared to the hvCTS assay, both in the absence of preloads. The hvCOC response was plotted as stroke work normalized to the untreated baseline at 1-Hz pacing; the hvCTS response was plotted as the developed force normalized to the untreated baseline at 1-Hz pacing. Data plotted as mean±SEM (hvCOC n=4 for both drugs; hvCTS n=5 for isoproterenol and n=4 for levosimendan).

FIG. 2B illustrates an exemplary setup that allows regulation of the luminal preload by adjusting the height of the fluid reservoir and thus altering the hydrostatic pressure load on the hvCOC. The developed pressure within the hvCOC lumen, generated by contraction, is recorded via a pressure transducer, synchronized with a high-speed video camera for simultaneously monitoring the change in chamber size, as an exemplary approach to monitoring chamber size, which is amenable to monitoring using a number of techniques. As shown, cardiac module 6 comprises media 5 in contact with cardiac organoid chamber 7. Tube 11 for exchanging fluid (e.g., media 5) and for housing pressure transducer wire 12 is in contact with cardiac organoid chamber 7. Fluid pressure is controlled by fluid elevator 8 (e.g., a jack), a media tank 9 disposed on the fluid elevator 8, and a media tube 10 for delivering media to the cardiac organoid chamber 7 via tube 11. Pressure is recorded using a pressure transducer connected via pressure transducer wire 12 to pressure recorded 13. The behavior of cardiac organoid chamber 7 is preserved by recording device 14.

FIG. 7A shows how the increase in preload is correlated with an increase in developed pressure when an hvCOC contracts, as predicted by the length/tension relationship in FIG. 1. FIG. 7B shows pressure/volume (PV) loops generated by hvCOC at preload of 0, 2.5, 5 and 7.5 mmH$_2$O: as preload increases, the area inside the PV loop increases, representing an increase in stroke work. Preload is physiologically relevant as the heart is filled with blood (known as the end-diastolic volume) prior to its contraction phase (systole), and the larger the end-diastolic volume (and the preload), the greater the contractile force (as stated by the Frank-Starling law of the heart). FIG. 7C shows an hvCOC being treated with increasing doses of levosimendan, a calcium sensitizer and known positive inotrope, at preload of 0 to 7.5 mmH$_2$O. With no preload (0 mmH$_2$O), the hvCOC showed no increase in developed pressure in response to 1 µM levosimendan. An increase in preload to 2.5 or 5 mmH$_2$O greatly enhanced the response of the hvCOC to levosimendan, showing an approximately 50% increase in developed pressure at 5 mmH$_2$O preload and 0.1 µM levosimendan. The change is also apparent when observing the pressure/volume relationship (FIG. 7D). At 7.5 mmH$_2$O, the developed pressure at untreated baseline was almost 1.5 mmH$_2$O, and did not show any significant dose-dependent increase upon addition of levosimendan (FIG. 7C), indicating that the optimal stretching for manifesting pharmacological responses could be close to $L_{max}$ but is determined empirically on a case-by-case basis.

FIG. 11. A) Schematic of fluidic exchange system for an organoid cartridge, including fluidic lines, pumps, valves, pressure transducer and fluid tanks. Specific configurations of valves and pumps are used depending on the function, such as B) aspiration or C) fresh media addition to the media bath. A detailed description of the illustrated embodiment of the bioreactor system is presented in Example 1.

FIG. 15. MATLAB analysis to generate average P-V loops from an acquisition. A) Calculation of mean volumetric contraction curve of a tissue. Each volumetric contraction of a beat is plotted as a scatter plot with the time of maximum contraction set to t=0 seconds. Mean curve is denoted as a solid red line. B) Line graph of mean P-V loop summarizing multiple contractions. Red circles denote values at sampled time points.

DETAILED DESCRIPTION

Figure 1:
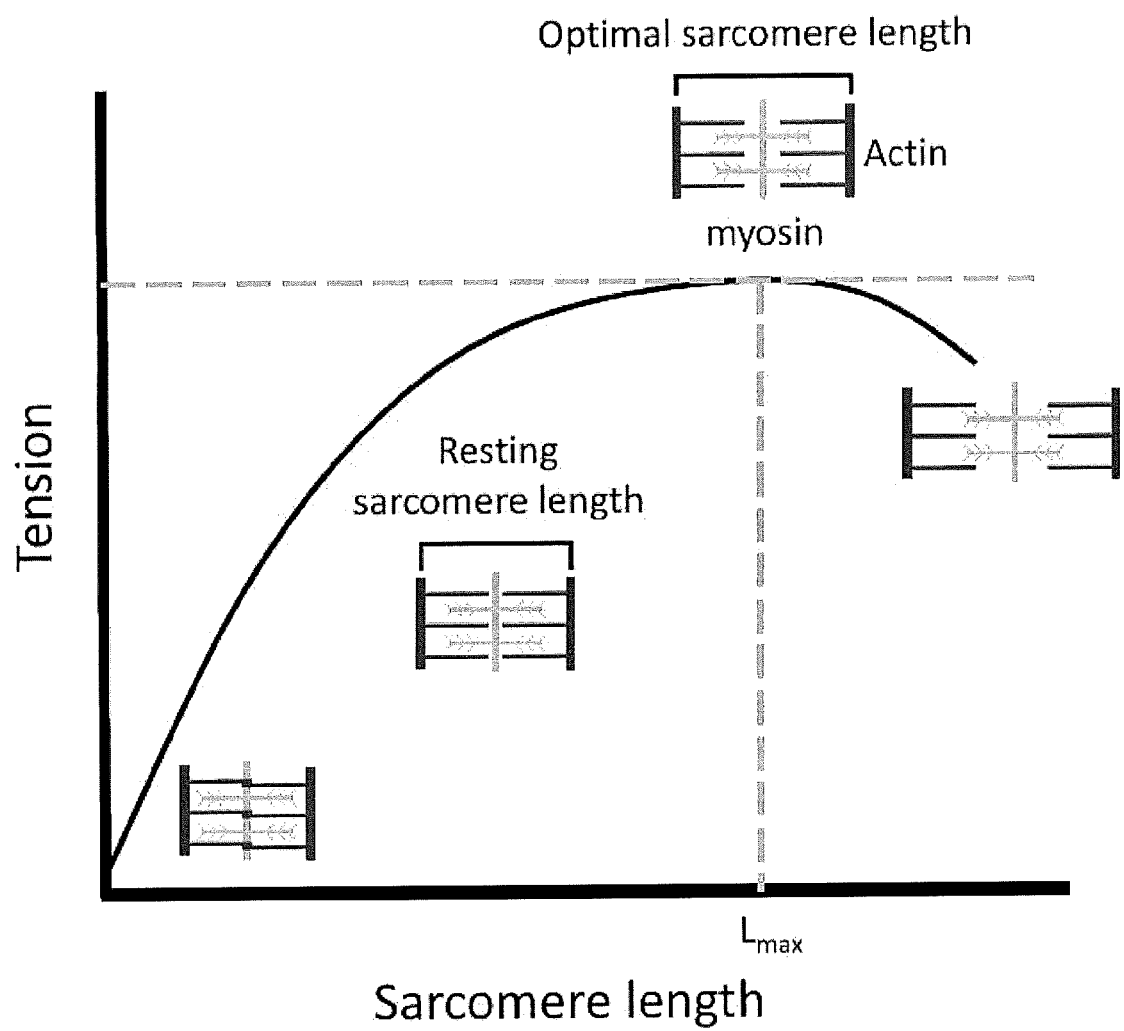
FIG. 1. Describes the relationship between length and tension in cardiac muscle. At resting length, the cardiac muscle maintains minimal tension, but as the muscle is stretched, the tension sharply rises with the overlapping actin and myosin filaments interacting to form cross-bridges and contract. The tension peaks at a length known as $L_{max}$, in which sarcomeres have optimal overlapping of actin and myosin filaments for cross-bridge formation. As the muscle is stretched beyond $L_{max}$, the degree of overlapping drops and consequently isometric tension also decreases.
Figure 2A:
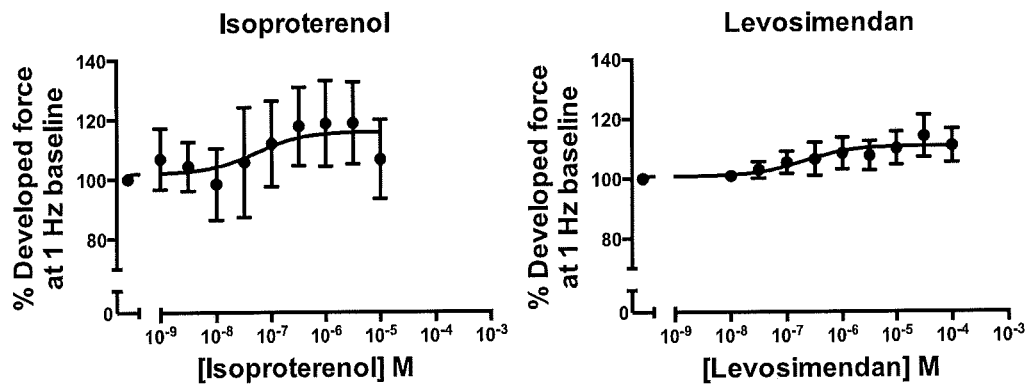
FIGS. 2A-2C. Describes the limited abilities of unstretched cardiac tissues to detect positive inotropy.
Figure 2B:
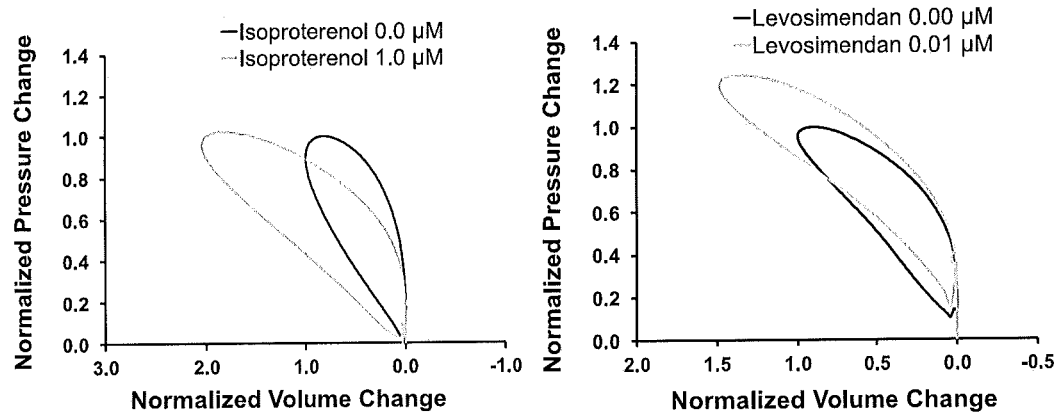
Figure 2C:
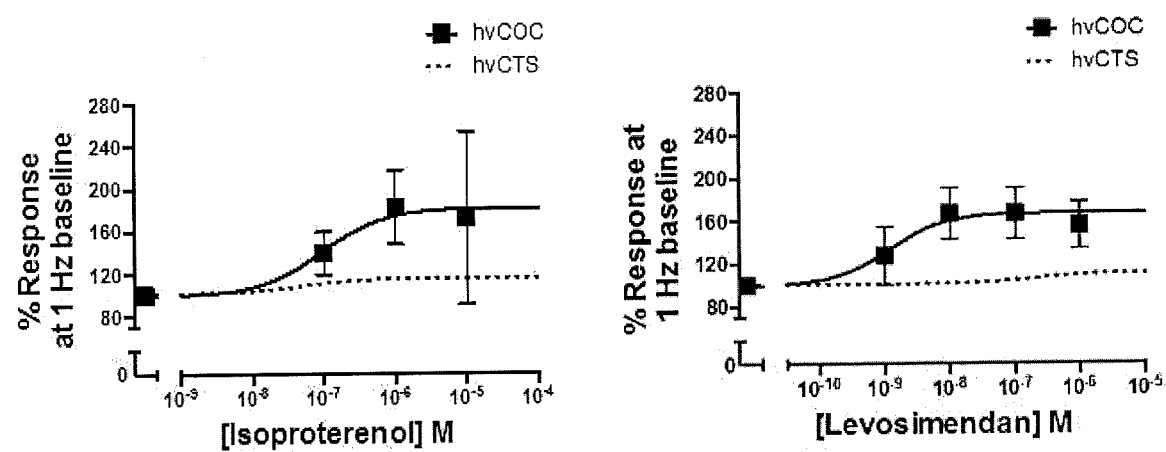
Figure 3:
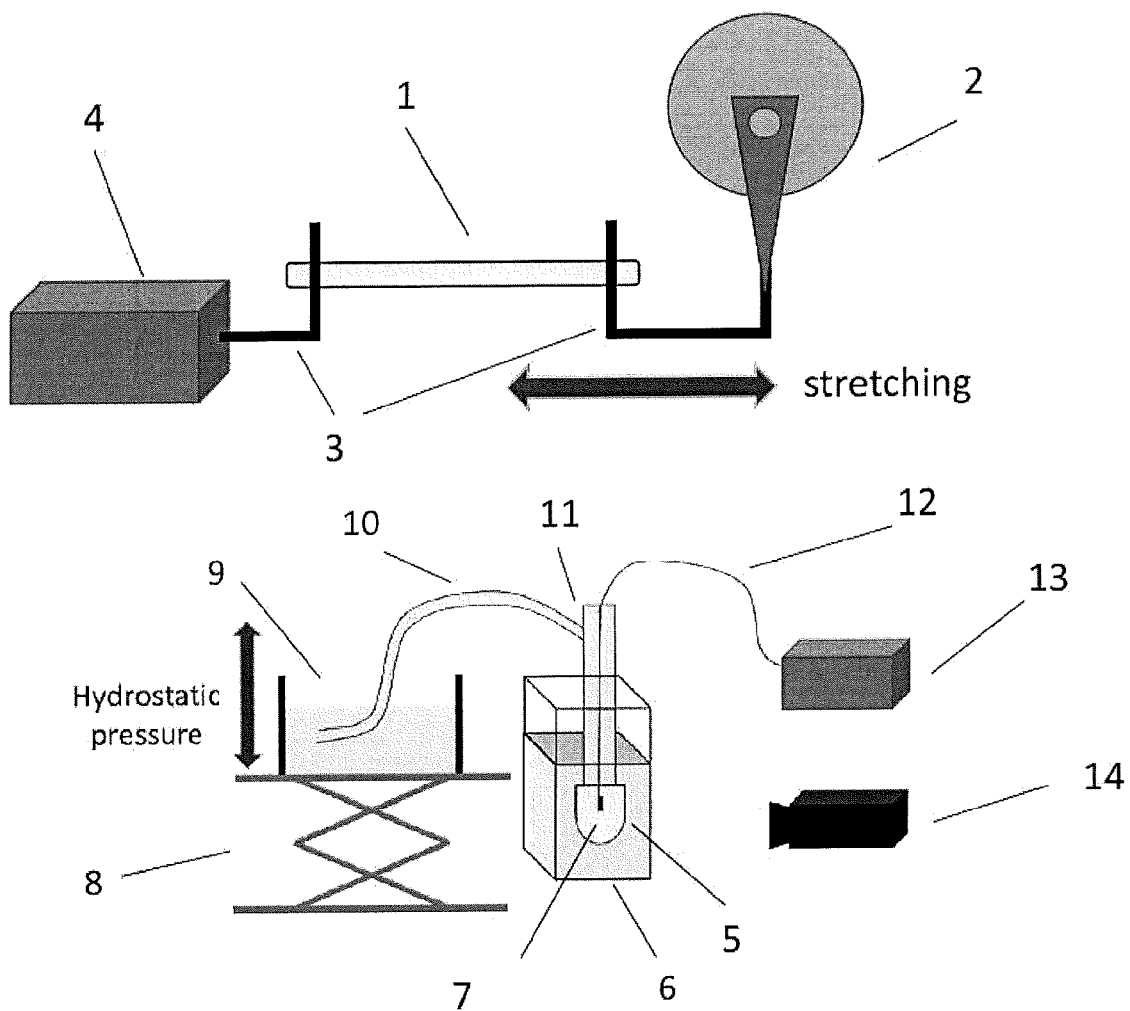
FIG. 3. Describes exemplary apparatuses in which cardiac tissues can be stretched to defined extents and their contractility measured. For linear tissues such as the human ventricular cardiac tissue strip, FIG. 2A describes an apparatus that can be used for length control. With the linear cardiac tissue affixed to two poles, one of which is fixed and the other of which is connected to a motor, the length of the tissue can be finely controlled by movement of the motor. Force generated by the tissue can be detected by various means such as a force transducer connected to the fixed pole. By restricting the muscle from shortening, the contraction is isometric, similar to that seen in the heart in early systole. As shown, a hydrogel comprising cardiomyocytes 1 is attached to two hydrogel supports 3. A mobile hydrogel support 3 is attached to motor 2 and the other hydrogel support 3 is attached to immobile anchor 4. For three-dimensional chamber-structured cardiac tissues such as the human ventricular cardiac organoid chamber.
Figure 4:
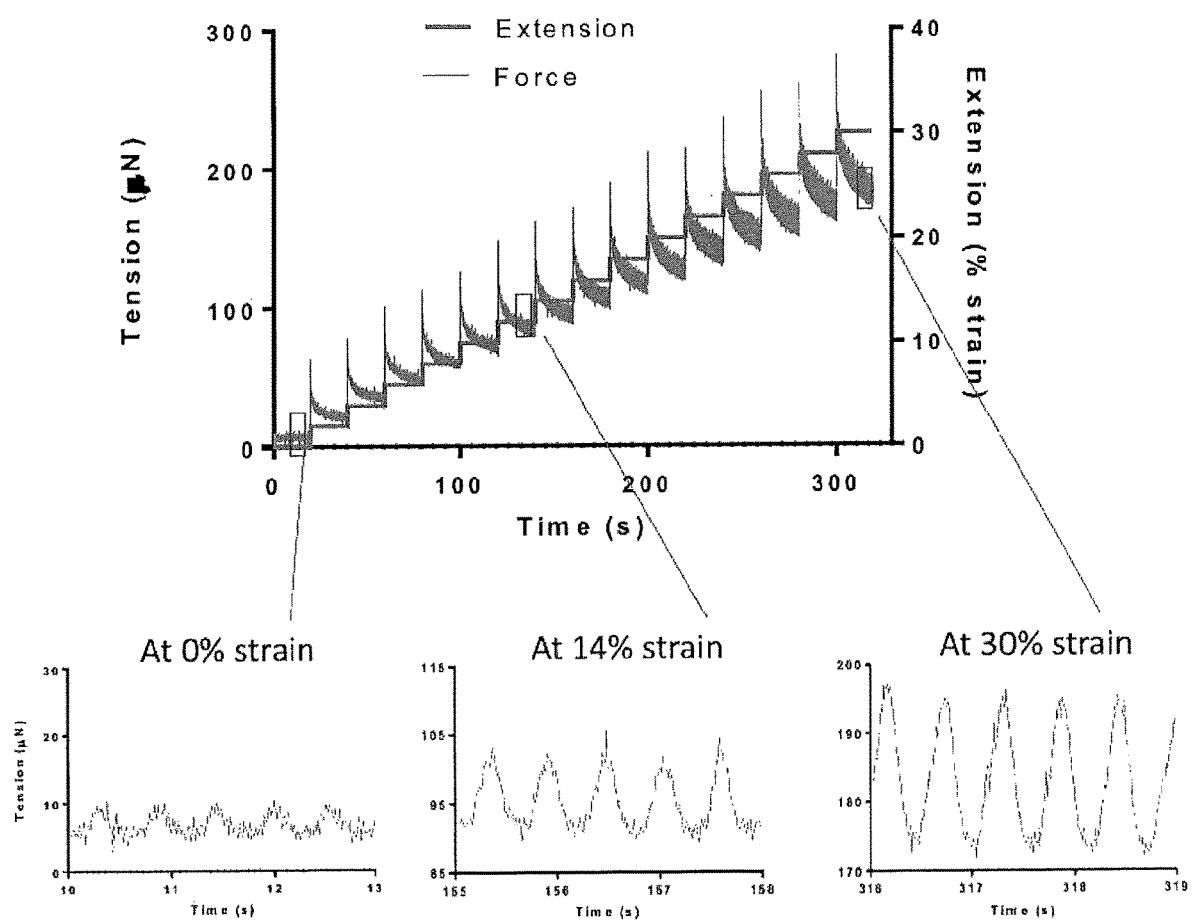
FIG. 4. Shows an exemplary recording from a hvCTS of tension over time: hvCTS was connected to an isometric muscle bath setup as in FIG. 2A, and the tissue length was adjusted by increasing it by 2% every 20 seconds, from 0% up to 30% strain (the increase in length is relative to the resting length of the tissue). As predicted by the theoretical length/tension relationship of cardiac muscle, the stretching induced substantial increase in static tension (as indicated by the troughs of the twitches, from about 5 μN at 0% strain to 172 μN at 30% strain) as well as developed tension (as indicated by the amplitude of the twitches, from about 5 μN at 0% strain to 20 μN at 30% strain). By plotting developed tension over length (or strain), the optimal length $L_{max}$ is determined for each hvCTS. Physiological responses are expected to be more apparent when the length of the hvCTS is close to $L_{max}$.

The disclosure provides materials and methods constituting an ex vivo model of human cardiomyocyte function that presents a number of advantages collectively resulting in the disclosed model system more accurately and precisely reflecting the in vivo behavior of human cardiomyocytes in three-dimensional organized forms of tissues and organs, e.g., the heart. Notable among the advantages of the disclosed model system is the incorporation of cardiomyocyte preload that allows the model to more closely mimic the behavior of cardiomyocytes in vivo, which are normally subjected to varying preloads that affect performance. More particularly, the application of controlled stretching to engineered cardiac tissues improves signal-to-noise ratios in contractility measurements. Applications that are positively affected by controlled preloading sufficient to increase signal-to-noise ratios include, but are not limited to, (a) augmenting inotropic responses of the tissues to pharmacological treatments, and (b) amplifying phenotypic differences between healthy and diseased states.

The engineered cardiac tissues useful in the disclosed model system include, but are not limited to, cardiac tissue strips and cardiac organoid chambers. Cardiac tissue strips according to the disclosure include, but are not limited to, human cardiac tissue strips, including human ventricular cardiac tissue strips. An exemplary human ventricular cardiac tissue strip is a human pluripotent stem cell-derived ventricular cardiac tissue strip. Cardiac organoid chambers according to the disclosure include, but are not limited to, human cardiac organoid chambers, including human ventricular cardiac organoid chambers. An exemplary cardiac organoid chamber is a human pluripotent stem cell-derived ventricular cardiac organoid chamber.

The cardiomyocyte model system disclosed herein is useful in assessing, or assaying, known or potential cardiac therapeutics for inotropic responses under real-world conditions involving cardiomyocyte preloading. The disclosed materials and methods are useful in assessing positive, negative, and null inotropic responses to known or candidate cardiac therapeutics. Moreover, the materials and methods are useful in assessing cardiac effects of any chemical compound, e.g., drug, under real-world conditions involving cardiomyocyte preloading. Thus, the disclosure provides materials and methods for the rapid, cost-effective, reliable and accurate assessment of the cardiac effects of any chemical compound, e.g., drug or therapeutic, including known or candidate therapeutics for affecting body functions and disease courses not directly involving the cardiovascular system as well as assessing known or candidate cardiac therapeutics. Thus, the disclosed materials and methods are used to assess known or candidate therapeutics for the treatment, prevention or amelioration of symptoms of a variety of diseases, including but not limited to dilated cardiomyopathy, hypertrophic cardiomyopathy, pulmonary atresia, Tetralogy of Fallot, dilated cardiomyopathy with ataxia, heterotaxy syndrome, Friedreich's ataxia (FRDA), Kearns-Sayre syndrome, carbohydrate-deficient glycoprotein syndrome type Ia (phosphomannomutase-2 congenital defect of glycosylation Ia or PMM2-CDG-Ia), spinocerebellar ataxia, Wilson disease, Dandy-Walker syndrome, Leigh disease, MELAS (mitochondrial encephalomyopathy, lactic acidosis, and stroke-like episodes), and MERRF (myoclonic epilepsy with ragged red fibers).

The disclosure provides a system and associated methods for screening compounds for beneficial or toxic cardiac effects in cardiomyocytes derived from healthy individuals, from cardiac patients, or from patients having a non-cardiac disease with cardiac effects, such as a neurological disease, disorder or condition that can have at least one cardiac effect. Some configurations of the system involve an efficacy screen followed by a toxicity screen, depending on the phenotype of the disease being modeled. An initial efficacy screen is deployed to identify treatments that ameliorate, rescue or abolish disease symptoms, followed by a toxicity screen to eliminate treatments with unacceptable deleterious side-effects.

The disclosure provides several in vitro cardiac tissue- or organoid-based models for assessing the efficacy and/or toxicity of known or candidate therapeutics, including cardiac therapeutics, and for assessing or monitoring the function or behavior of cardiac tissue or organoids of patients with cardiac disease or patients with non-cardiac disease having at least one cardiac effect. The bio-hybrid material provides the significant benefit of making available in vitro assays that more accurately reflect in vivo physiological effects. In some embodiments, the system comprises a Cardiac Tissue Strip (CTS), such as a human ventricular Cardiac Tissue Strip (hvCTS) supported in a manner that allows for significant flexibility in movement of the gel, with an associated detection (e.g., recording) device to capture gel movement in the presence or absence of a test compound. To facilitate preloading, an hvCTS is supported at least at two points, one of which is fixed in space and associated with an attached force transducer. At least one other support point, e.g. a pole, is attached to a motor to allow for precisely controlled movement resulting in the stretching of the hvCTS. The CTS itself is simple to prepare, essentially involving tissue-forming cardiomyocytes embedded in a biocompatible gel. The hvCTS system and method are amenable to high-throughput formats as well as conventional formats.

Another in vitro assay system and method involves a tissue or organoid chamber developed and maintained in an organoid cartridge typically located in an organoid module, as described herein. The assay involves exposure of a tissue or organoid, from a healthy or diseased individual, to a known therapeutic or a candidate compound in a cartridge placed in an environment where a detection (e.g., recording) device can monitor organoid behavior. The environment also typically provides for the delivery and removal of fluid such as media and compound-containing fluid under controlled conditions, with various controls needed to maintain an environment compatible with tissue or organoid viability. The system and method reveal compounds having beneficial cardiac effects at the cellular, tissue and/or organoid or organ level, increasing the accuracy and reliability of results obtained in screens for compounds having such effects. Moreover, this assay can be scaled up to use more than one hvCOC. The multiple tissues and/or organoids, which may be of the same type (e.g., cardiac) or different, are developed and maintained in distinct organoid cartridges that may conveniently be located in a single organoid module (it is understood that organoid cartridges and organoid modules may contain tissues or organoids). In some embodiments, this arrangement conveniently allows for a single mirror system such as a pyramidal mirror system, to be used in conjunction with a single detection (e.g., recording) device. The disclosure also contemplates combining the assays, which reveals information about the cardiac effects of a known or candidate compound on healthy or diseased cells as well as the effects of a known or candidate compound on one or more cognate tissues, organoids or organs, or on a plurality of different tissues, organoids or organs. Performing more than one assay on one or more samples from a given source further strengthens the data obtained in terms of accuracy, reliability and reproducibility, with a manageable addition to cost in terms of money and time.

The following quoted terms are expressly defined herein.

"APD50" means the action potential duration at 50% repolarization.

"APD90" means the action potential duration at 90% repolarization.

"FRDA" means Friedreich's ataxia.

"FXN" means the protein frataxin, while "FXN" means a polynucleotide encoding FXN.

An "engineered cardiomyocyte" is a cardiomyocyte that has been recombinantly engineered to exhibit a particular genotype and phenotype. As used herein, the typical engineered cardiomyocyte comprises a cardiomyocyte into which an exogenous nucleic acid, such as a short hairpin RNA against FXN, is introduced using any known vector, such as a lentiviral vector as disclosed herein.

"hESC" means a human embryonic stem cell, and "hESCs" means a plurality of human embryonic stem cells.

"hiPSC" means a human induced pluripotent stem cell, and "hiPSCs" means a plurality of human induced pluripotent stem cells.

"hPSC" means a human pluripotent stem cell, which can mean either an hESC or an hiPSC, and "hPSCs" means a plurality of human pluripotent stem cells.

"hvCM" means a human ventricular cardiomyocyte, and "hvCMs" means a plurality of human ventricular cardiomyocytes.

"hvCOC" means a human ventricular cardiac organoid chamber, and "hvCOCs" means a plurality of human ventricular cardiac organoid chambers.

"hvCTS" means a human ventricular cardiac tissue strip, and "hvCTSs" means a plurality of human ventricular cardiac tissue strips.

In general, the disclosure contemplates a variety of assay formats to assess known or candidate therapeutics useful in treating a variety of diseases, including cardiac and non-cardiac diseases. The assay formats involve the assessment of effects of the known or candidate therapeutics on preloaded cardiac tissue or organoids. Preloading cardiac tissue or organoids, e.g., by stretching the cardiac tissue or organoid, more closely reflects the in vivo state of cardiac tissues and organs, leading to more sensitive and accurate measures of the cardiac effects of known or candidate therapeutics. One assay format provides preloaded cardiac tissue as a human ventricular Cardiac Tissue Strip (hvCTS) amenable to rapid high-throughput assays for cardiac effects of known or candidate therapeutics. Another assay format provides a preloaded cardiac organoid, e.g., a human ventricular Cardiac Organoid Chamber (hvCOC), which permits an assessment of the effect or effects of a known or candidate therapeutic on the three-dimensional biomaterial known as a cardiac organoid. By modeling the three-dimensional heart, the hvCOC assay format is expected to provide information on known or candidate therapeutics that will translate to the in vivo heart condition better than known cardiac assay formats, identifying efficacious compounds with acceptable toxicity profiles more quickly and cost-effectively than using known technologies.

The cardiac assay formats disclosed herein are useful for assessing known or candidate cardiac therapeutics useful in treating any of the various known cardiac diseases or conditions. The cardiac assay formats are also useful in assessing the cardiac effects of known or candidate therapeutics for the treatment of non-cardiac diseases or conditions that might have cardiac effects. Known or candidate therapeutics for various diseases are contemplated as suitable compounds for assessment using the preloaded cardiac tissue(s) or organoid(s) of the assay formats disclosed herein. Those diseases/conditions include, but are not limited to, dilated cardiomyopathy, hypertrophic cardiomyopathy, pulmonary atresia, Tetralogy of Fallot, heterotaxy syndrome, Friedreich's ataxia (FRDA), Kearns-Sayre syndrome, carbohydrate-deficient glycoprotein syndrome type Ia, spinocerebellar ataxia, Wilson disease, Dandy-Walker syndrome, dilated cardiomyopathy with ataxia, Leigh disease, MELAS (mitochondrial encephalomyopathy, lactic acidosis, and stroke-like episodes), and MERRF (myoclonic epilepsy with ragged red fibers), neurological diseases or disorders, and ataxias, with cardiac dysfunction, e.g., neurological diseases or disorders that perturb the neurocardiac axis. Hereditary neurological diseases and disorders can have direct or indirect cardiovascular effects, including effects on the physiological functioning of the heart. Exemplary neurological diseases and disorders having the potential for such effects include, but are not limited to, Friedreich's ataxia (FRDA), Kearns-Sayre syndrome, which is a mitochondrial myopathy with cardiac conduction abnormalities and cardiomyopathy; carbohydrate-deficient glycoprotein syndrome type Ia, which is a neurological disease with dysmorphy and cardiac manifestations (mean onset of cardiac involvement is 5 months, 20% die within first year of life, often due to serious cardiac complications); spinocerebellar ataxias, which have cardiovascular abnormalities, particularly abnormal heart rate variabilities; Wilson disease, which is a copper metabolism disorder with concentric remodeling and supraventricular tachycardia; arrhythmias; Dandy-Walker syndrome, which is characterized by cardiac malformations; dilated cardiomyopathy with ataxia, which exhibits DCM and long QT with 70% of patients progressing to cardiac failure or sudden cardiac death; Leigh disease, which is a neurological disorder that can be associated with hypertrophic cardiomyopathy; MELAS, which is a mitochondrial disease with LV hypertrophy; and MERRF, which is a neuromuscular disorder with cardiomyopathy.

In order to sustain energy consumption required by constant cardiac contractions, cardiomyocytes—the individual working units of the heart—are endowed with the highest mitochondrial density of all cells.[26] FRDA, as an exemplary non-cardiac disease that has deleterious effects on the heart, is caused by a genetic mutation that decreases the production of FXN, and consequently biosynthesis of numerous iron-sulfur proteins that are critical for oxidative metabolism in the mitochondria. Consequently, the disease is expected to adversely affect cardiomyocytes, which depend predominantly on mitochondrial ATP production. Not surprisingly, heart failure and arrhythmia are the major causes of mortality in FRDA patients[3-6], indicating contractile and electrophysiological dysfunction at the cellular level. In the experimental work disclosed herein, the effects of FXN expression on contractile and electrophysiological function in hvCM models generated either from hESCs or hiPSCs were tested, with the hiPSCs including lines reprogrammed from FRDA-patient cells. Indeed, FRDA-hiPSC lines of two distinct patients both showed lower FXN transcripts and proteins than healthy hESCs and hiPSCs, indicating hvCMs from FRDA-hiPSCs provide a model for studying FRDA in vitro.

To eliminate possible differential responses in contractile and electrophysiological functions attributed to variations in genetic background from different hPSC lines, an isogenic FRDA model was generated by knocking down FXN expression in hESCs, using lentiviral delivered Lv-shFXN, to mimic the low FXN expression as reported in FRDA patients, as disclosed in the following examples. This strategy had proved to be effective, as demonstrated by reduction of FXN expression at both the transcript and protein level (Example 3). More importantly, for the first time, contractile dysfunction was observed in cardiac tissue hvCTS engineered from FXN-deficient hvCMs. Unlike healthy hESC-hvCTS that showed progressive increase in developed force over time, contractile force was reduced and remained low in FXN-deficient hESC-hvCTS (Example 3). Moreover, the upstroke and decay velocities of force developed were also slower in FXN-deficient hESC-hvCTS. These observations suggest that the lack of FXN affected the ability of hvCMs to generate force, which became more obvious as the hvCTS matured over time.

Effects of FXN deficiency on cardiac contractile dysfunction were further validated in an FRDA-hiPSC-derived hvCM model. Similar to the isogenic FXN-deficient hESC-hvCM model, FRDA-hiPSC-derived hvCMs also demonstrated reduced synthesis of FXN by qPCR and Western blot, relative to healthy hiPSC-hvCM control, despite differences in genetic background between the cell lines. The relationship between developed force and FXN expression was validated by six different hESC- and hiPSC-hvCTS models for FRDA, including isogenic FXN knockdown models in healthy hESC- and hiPSC-hvCTSs, their respective healthy hESC- and hiPSC-hvCTS controls, and FRDA patient-derived hiPSC-hvCTSs from two patients. It is important to note the strong positive correlation between the magnitude of active force and FXN expression (Example 4), as indicated by Pearson's coefficient of 0.84, where a value of >0.5 indicates a strong positive correlation. Hence, the data disclosed herein establish, for the first time, the FRDA contractile phenotype in two types of in vitro models, i.e., an isogenic model from FXN knockdown and another model derived directly from an FRDA patient with an intrinsic mutation of the FXN gene.

Restoration of FXN Expression Rescued Compromised Contractile Function

Figure 5:
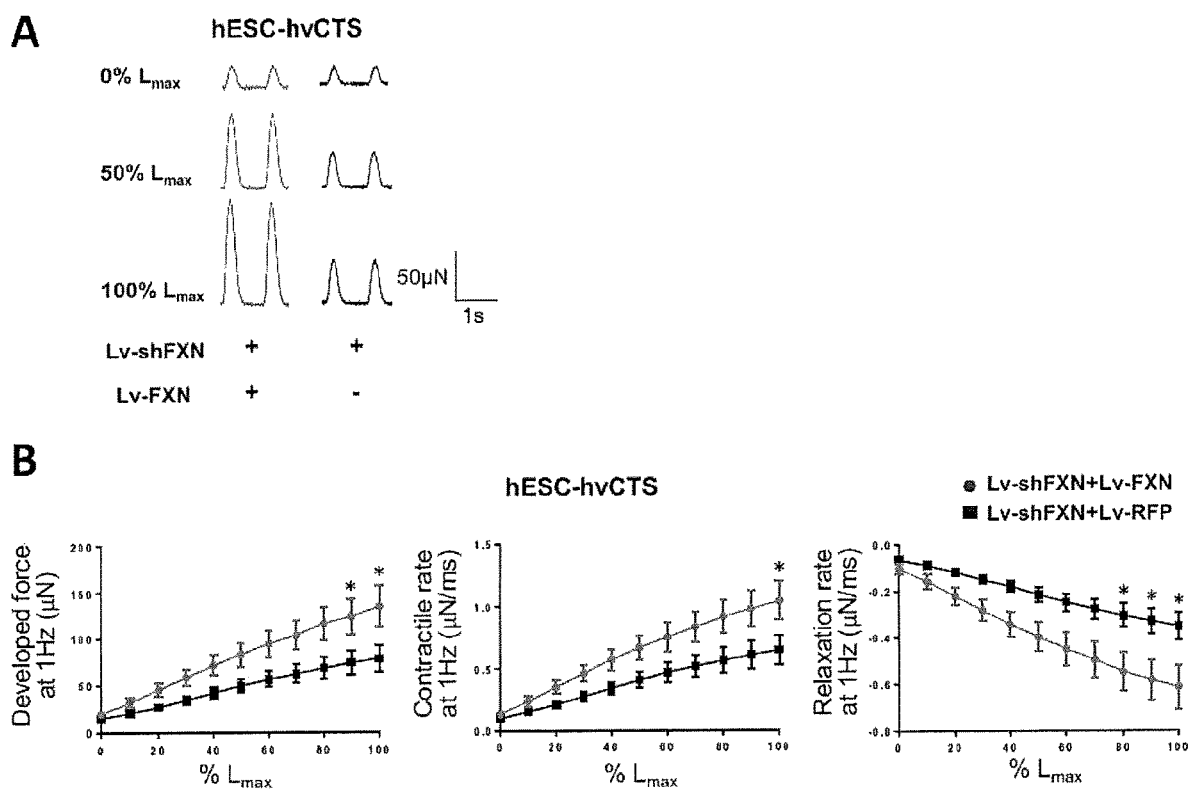
FIG. 5. Shows an example of how physiomimetic length control can manifest disease phenotypes which are otherwise not apparent in unstretched tissues. Human embryonic stem cell-derived hvCTS, transduced with a lentiviral vector carrying short hairpin RNA (shRNA) that suppresses the expression of mitochondrial protein frataxin (FXN), is used as a disease model for the hereditary neuromuscular disorder Friedreich's Ataxia (FRDA). shFXN-transduced hvCTS shows weak contractile force (less than 20 μN when unstretched), as anticipated from phenotypes observed in clinical FRDA patients, who also express lower levels of FXN than healthy individuals. The restoration of FXN expression, by co-transduction of shFXN together with a lentiviral construct carrying a constitutively expressing FXN transgene (Lv-FXN), was anticipated to rescue the contractile deficit. At 0% strain, the rescue effect was not observed, with no significant difference (p<0.05, Student's t test) between the shFXN+Lv-FXN group versus the shFXN+RFP control group (FIG. 5A). At 50% $L_{max}$, the difference between the two groups became more evident (FIG. 5A), whereas the difference in developed force reached statistical significance when the hvCTS was stretched to 90% $L_{max}$ or above (FIG. 5B). The contractile and relaxation kinetics of the hvCTS also showed significant differences between the 2 groups only at $L_{max}$ and over 80% $L_{max}$, respectively, indicating that the optimal sarcomere length represented by $L_{max}$ mimics a physiological state that can manifest otherwise hidden disease phenotypes.

By inducing expression of FXN in FRDA-patient hiPSC and FXN-knockdown hESC FRDA models, the force generated in hvCTS from both models was significantly improved, demonstrating for the first time, rescue of compromised contractile function in human FRDA three-dimensional tissue models by restored expression of FXN (FIG. 5, Example 6). This is in agreement with the inducible and reversible murine FRDA model demonstrating restoration of FXN expression can reverse pathological effects.[16] These findings indicate restoration of FXN expression is an effective strategy for treating FRDA patient by preventing and reversing pathological cardiac symptoms that are major contributors to fatality for FRDA patients. Importantly, the work disclosed herein demonstrated that three-dimensional human pluripotent stem cell-derived tissues, with appropriate selection of sensitive readouts as had shown using an isometric force measurement system, serve as sensitive and accurate disease models for therapeutic testing and drug screening.

FXN-Deficient hvCOC Models

Figure 6:
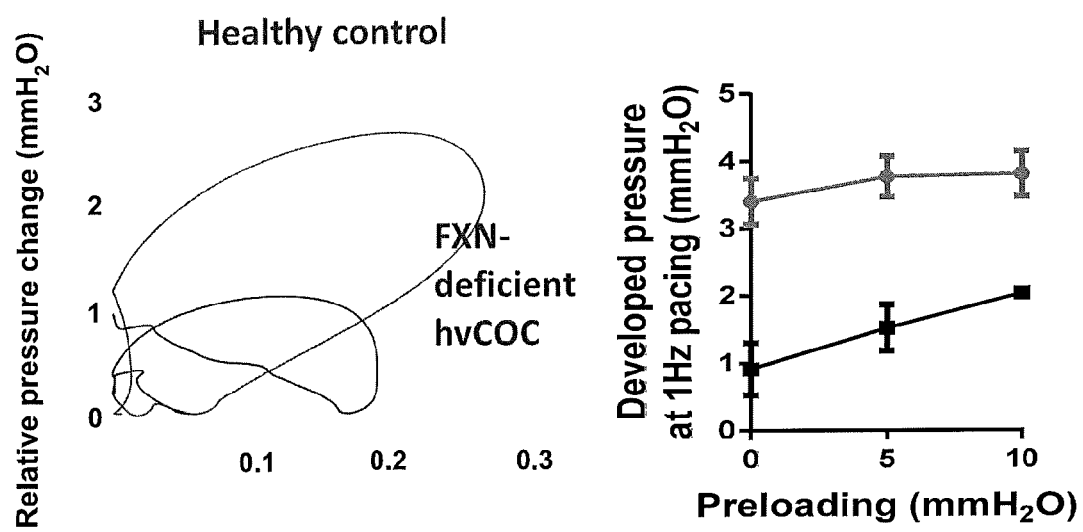
FIG. 6. Shows the effect of preload on the developed pressure of healthy and FRDA-carrying hvCOC at 1-Hz pacing. (Left) Representative pressure-volume loops of healthy control hESC-hvCOC and FRDA hiPSC-derived hvCOC, with the latter having a smaller area than the former. (Right) Developed pressure of both healthy and FRDA disease-carrying hvCOCs show an increase with increasing preload, as expected (mean±SEM, n=2-3).

In addition to hvCTS, fluid-ejecting human ventricular cardiac organoid chambers (hvCOC) provides a higher-order engineered cardiac tissue for modeling FRDA disease phenotypes. The hvCOC model can recapitulate physiologically complex behaviors such as pressure-volume relationships, stroke work and cardiac output, and also provides a pro-maturation milieu to enhance the cardiomimetic properties especially as it relates to contractility. Patient-derived FRDA hiPSC-hvCMs, are physically intact and can pump fluid and generate pressure (FIG. 6). These models showed compromised functional properties, including stroke work, stroke volume, ejection fraction, developed pressure and cardiac output, when compared with control hESC-hvCOCs, both under baseline conditions or with 5 and 10 mm $H_2O$ preload (FIG. 6). They add a higher-tier assay for treatments that produce positive results in the hvCTS disease models, providing a more physiological and mature tissue construct with higher sensitivity in confirming positive effects on contractility.

The following examples illustrate embodiments of the invention. Example 1 describes the directed differentiation of pluripotent stem cells to form ventricular cardiomyocytes and the engineered tissue fabrications of the systems and assays disclosed herein. Example 2 describes experiments with the preloading of cardiomyocytes used in the disclosed systems and methods, with the preloading accomplished by cell/tissue/organoid stretching by electromechanical translation or by pressure changes. Examples 3-5 provides general disclosures relating to the cardiomyocyte assay formats disclosed herein, i.e., cardiomyocyte tissue strip (CTS) and cardiomyocyte organoid chamber (COC), respectively.

EXAMPLES

Example 1

Direct Cardiac Differentiation and Engineered Cardiac Tissue Fabrication

Ventricular (v) cardiomyocytes (CMs) were differentiated from human pluripotent stem cells (hPSCs) as previously reported[50]. All vCMs described herein originated from human embryonic stem cell (hESC) line HES2 (NIH code: ES02).

At day 15 post-differentiation, the vCM cardiospheres were dissociated with 0.025% trypsin-EDTA. The dissociated vCMs were then resuspended in StemPro-34 complete medium with 50 μg/ml ascorbic acid and 10 μM Y-27632 dihydrochloride.

Fabrication of Human Ventricular Cardiac Tissue Strip (hvCTS) and Cardiac Organoid Chamber (hvCOC)

Seventy-two hours after dissociation, the hvCTS was made by mixing 1.3 million hESC-vCMs and 0.13 million human foreskin fibroblasts, together with 110 μl collagen gel comprising 1.67 mg/ml collagen and 72.3 mg/ml Matrigel. The cell mixture was then cast into a PDMS mold with two pillars and allowed to solidify for 2 hours in a 37° C., 5% $CO_2$ incubator. Then, the cell mixture was fed with 7 ml DMEM medium (high glucose) supplemented with 10% newborn calf serum. Half of the medium was changed every 2 days.

The hvCOC was made by a similar approach: Ten million hESC-vCMs and 1 million human foreskin fibroblasts were mixed with 1650 μl collagen gel (same relative composition as described above for hvCTS). The mixture was then cast into a 13-mm diameter cavity in a 2% agarose gel. A modified 6-Fr silicone balloon Foley catheter (Cook Medical) was then inflated and placed into the center of the bioreactor to form the inner boundary of the hvCOC. An 8 mm porous polyethylene ring (Fisher Scientific) and a 6 mm rubber ring were placed on top of the catheter to provide an hvCOC anchor. The polyethylene ring, rubber ring and the catheter were held by a metal tube with 3.9 mm outer diameter. The cell mixture was allowed to solidify for 2 hours in a 37° C., 5% $CO_2$ incubator. Then, the solidified cell mixture was fed with 7 ml DMEM medium (high glucose) supplemented with 10% newborn calf serum. After 24 hours, the medium was aspirated and the agarose gel was removed. Twenty ml of medium was replenished and half of the medium was changed every 2 days. Further description of the hvCOC is provided in Example 5.

Example 2

Preloading Experiments with hvCTS

For rescue in the FRDA hvCTS disease model, hESC-vCMs were transduced with lentiviral shRNA targeting FXN (Lv-shFXN comprising shRNA sequence TRCN0000006137 in pLKO.1 vector backbone, Sigma) together with a second lentiviral construct, with the second construct containing either a constitutively expressed FXN transgene (Lv-FXN; GE Dharmacon OHS5835-EG2395) or Red Fluorescent Protein as a control (Lv-RFP; GE Dharmacon). Lv-shFXN is transduced at a multiplicity of infection (MOI) of 2, and Lv-FXN or Lv-RFP at MOI of 5, into dissociated hESC-vCMs after 24 hours of dissociation. The transduced hvCMs were assembled into hvCTS as described above.

On day 17 post-fabrication, human ventricular Cardiac Tissue Strips (hvCTS) were transferred from their molds and hooked to the force transducer unit and motor unit of an isolated muscle bath system (Aurora Scientific). The length of the hooked tissue was then adjusted to reach minimal developed tension, which was defined as the original length (Lo, or 0% $L_{max}$) of the tissue. The hvCTS was then incubated in the bath at 37° C. for 10 minutes. Next, the hvCTS was electrically paced (at 5V/cm) at 1 Hz frequency, and stretched from 0 to 50% strain in 2.5% increments every 20 seconds. Recordings were made using Dynamic Muscle Control software (Aurora Scientific). The contractile parameters at each % strain, such as developed force, contractile rate and relaxation rate, were analyzed by Clampfit (Molecular Devices). The length with the maximum developed force was defined as $L_{max}$. The contractile parameters were plotted against % $L_{max}$ using the linear interpolation method.

Preloading Experiments with hvCOC

Human ventricular Cardiac Organoid Chamber (hvCOC) behavior was measured on day 10 post-fabrication. First, the catheter was deflated and removed. Then, the culture medium was replaced by phenol red-free DMEM (with 25 mM glucose and 25 mM HEPES). Rubber tubing was then filled with medium and used to connect the metal tube of the hvCOC apparatus to a medium tank. The hvCOC was electrically paced at 1.5 Hz (5V/cm) and the pressure-volume change resulting from the paced contractions was recorded for 30 seconds. Pressure was measured by a pressure sensor (Millar) placed inside the hvCOC, and associated area change of the hvCOC was captured by high-speed camera (Allied Vision). The medium tank level was then adjusted from 0 mm (relative to medium level of that in the hvCOC bioreactor), to 2.5, 5 and 7.5 mm above the medium level (representing 0, 2.5, 5 and 7.5 mm $H_2O$ preload). The measurements at all 4 preloads (0, 2.5, 5 and 7.5 mm $H_2O$) were then repeated at each dose (0.01 and 0.1 µM) of levosimendan after a 5-minute incubation period.

Example 3

Cardiomyocyte Tissue Strips

The disclosure provides a cardiomyocyte tissue strip (CTS) useful in assaying known or candidate therapeutics for the treatment of a cardiac disease or disorder, or for the treatment of a non-cardiac disease or disorder having at least one cardiac effect, such as various neurological diseases, e.g., Friedrich's Ataxia (FRDA). In general, the CTS comprises a biocompatible gel comprising a plurality of cardiomyocytes and a biocompatible support apparatus for suspending the biocompatible gel, wherein the biocompatible gel and the biocompatible support apparatus form a cardiac tissue strip, a detection device for detecting movement of the biocompatible gel; and an electrical power source for applying an electrical pacing stimulus to the biocompatible gel.

The cardiomyocytes in the CTS may be human cardiomyocytes, such as human ventricular cardiomyocytes. Moreover, the human cardiomyocytes may be derived from at least one human pluripotent stem cell. In some embodiments, the cardiomyocytes are present at a concentration of at least $10^6$ cells/ml. In some embodiments, the biocompatible gel comprises matrigel, such as biocompatible gels wherein the matrigel is present at a concentration of at least 0.5 mg/ml or 1 mg/ml. The matrigel can be obtained from stock solutions containing, e.g., at least 5 mg/ml or at least 10 mg/ml matrigel. In some embodiments, the biocompatible gel further comprises collagen. The disclosure also provides embodiments wherein the collagen is type I human collagen. Some embodiments comprise biocompatible gels wherein the collagen is present at a concentration of at least 1 mg/ml, such as a concentration of about 2 mg/ml.

The support apparatus is contemplated as including at least two vertical support members (e.g., two vertical support members), and those vertical support members may be made of polydimethylsiloxane. In some embodiments, the vertical support members (e.g., two vertical support members) are approximately circular in cross-section with a diameter of about 0.5 mm. In some embodiments, the cardiac tissue strip is about 26.5 mm in length by about 16 mm in width by about 6 mm in height, such as a cardiac tissue strip that is 26.5 mm in length by 16 mm in width by 6 mm in height. In some embodiments, the detection device is a high-speed camera.

The disclosure also provides methods of making a cardiac tissue strip comprising: (a) providing a biocompatible mold of suitable dimensions, such as approximately 26.5 mm in length by approximately 16 mm in width by approximately 6 mm in height; (b) forming a biocompatible gel conforming to the mold, wherein the biocompatible gel comprises matrigel, collagen and a plurality of cardiomyocytes; and (c) affixing at least two vertical support members to the biocompatible gel, thereby forming a cardiac tissue strip. In some embodiments of the method, the vertical support members are affixed to the biocompatible gel by embedding the vertical support members in the biocompatible gel formulation prior to gelation. In some embodiments, the vertical support members are affixed to the biocompatible gel by adhesion or by mechanical attachment.

Example 4

Bioreactor

The disclosure provides a bioreactor used to culture many, and in some cases a variety of, tissue-engineered human organoids. The device was designed to allow interconnection and simultaneous measurement of multiple organoids, with features that enhance reproducibility and efficiency in organoid function testing by enabling subsequent characterizations to be performed within the same bioreactor with minimal manipulation or intervention by the operator.

Figure 7:
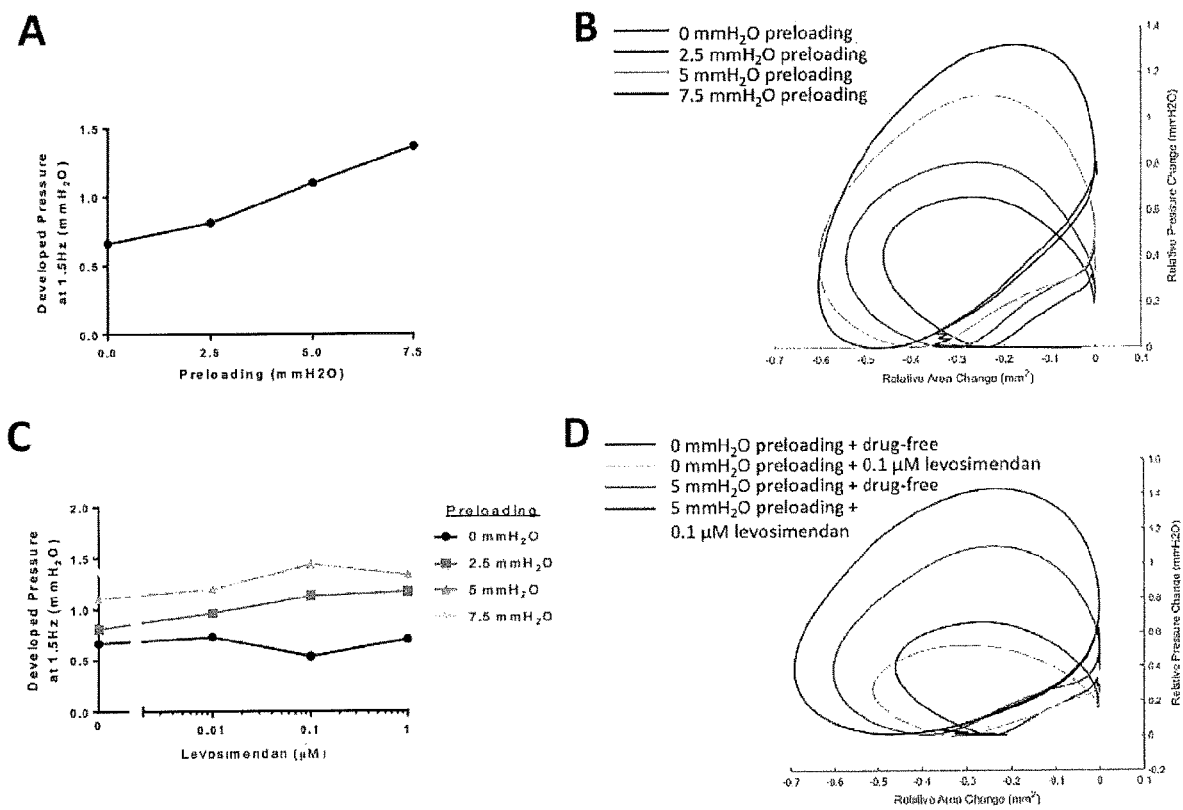
FIG. 7. Shows an example of how physiomimetic stretching in a human ventricular cardiac organoid chamber (hvCOC) can augment contractile responses to positive inotropic agents.

FIG. 7 provides a high-level schematic view illustrating the versatility of the disclosed bioreactor system. FIG. 7A shows an organoid module 10 which contains at least one organoid cartridge 20. An organoid cartridge 20 contains a single organoid 1 of any type (e.g., heart, brain, nerve, liver, kidney, adrenal gland, stomach, pancreas, gall bladder, lung, small intestine, colon, bladder, prostate, uterus, blood, vascular, tumor, eye, or skin, and the like). An organoid module 10 may contain multiple organoid cartridges 20, and thus may contain multiples of a single type of organoid 1 or a variety of organoids 1. The organoid module 10 is oriented such that a detection/recording device 2, e.g., a camera, can detect and record the contents of the organoid module 10, such as by having a face of the organoid module 10 closest to detection/recording device 2, and preferably perpendicular to the device, be substantially or completely transparent to at least one wavelength of the electromagnetic spectrum detected by detection/recording device 2. FIG. 7B presents a data processor 5, e.g., a computer, in connection with at least one organoid module 10. The organoid modules 10 are typically in 1:1 correspondence with the detection/recording devices 2, and the detection/recording devices 2 are in electronic communication with data processor 5 via communication path 7, e.g., either conventional electrical wiring or by wireless communication. Video monitor 6 may also be connected to data processor 5 via communication path 7.

Figure 8:
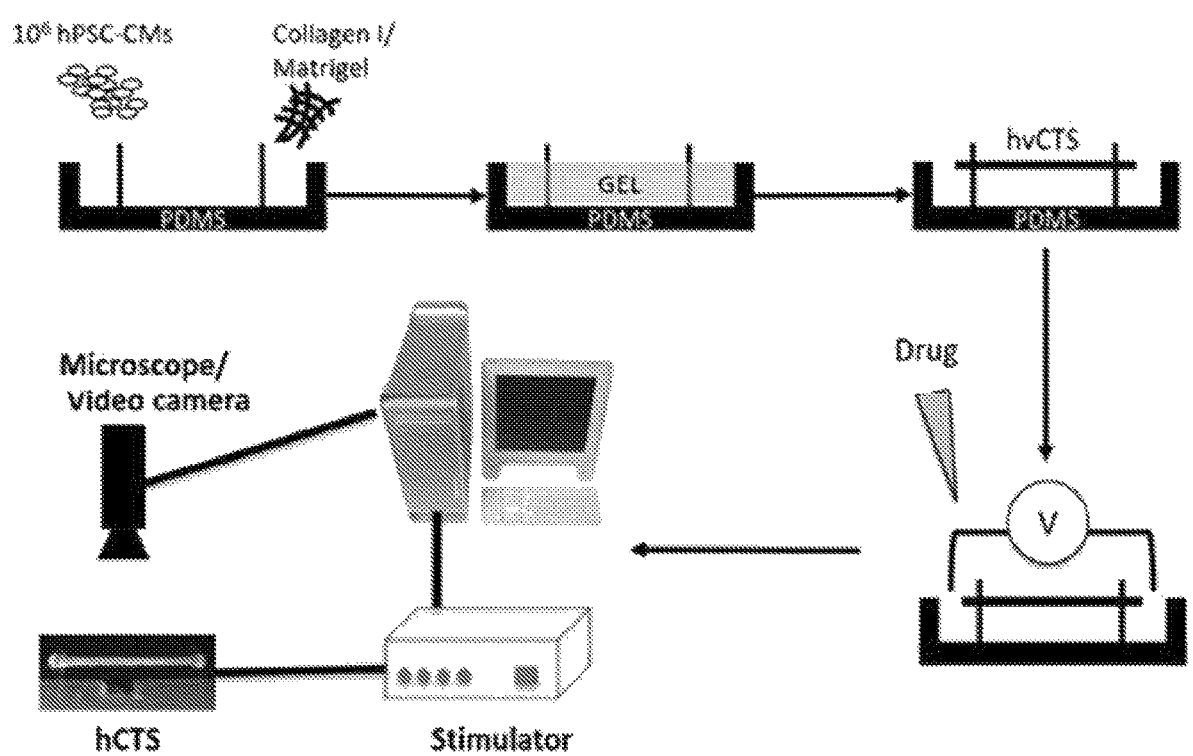
FIG. 8. A schematic illustration of the formation and use of a cardiomyocyte tissue strip (CTS). Following the depicted flowchart, panel 1 illustrates the addition of human pluripotent stem cell-derived cardiomyocytes and a collagen/Matrigel composition disclosed herein to a mold of polydimethylsiloxane (PDMS) containing two PDMS supports. Panel 2 shows the formed CTS. Panel 3 reveals the CTS extracted from the mold and positioned such that the biocompatible gel comprising cardiomyocytes is supported by the PDMS supports. Panel 5 shows the administration of drug to the CTS along with the application of an electrical stimulation illustrated by a voltage differential across the gel. Panel 5 shows the equipment used to monitor and record the response(s) of the CTS to the drug and electrical stimulus.

FIG. 8 presents a perspective view of an organoid module 10. Within organoid module 10 is located at least one organoid cartridge 20. Disposed within, or without (not shown), organoid module 10, and disposed within (not shown), or without, organoid cartridge 20 is mixer 19, such as a movable platform (e.g., shaker or rotating platform) on which organoid module 10 is placed or a magnetic stirring device (e.g., stir bar) located inside or outside organoid cartridge 20. In some embodiments, located within organoid module 10 is at least one light source 12 for illuminating organoid 1. Also located within organoid module 10 is at least one mirror 13 for directing electromagnetic radiation in the form of direct and/or reflected light images from organoid 1 to detection/recording device 2. In some embodiments, mirror 13 is a pyramidal mirror 13 to direct images from multiple organoid chambers 20 to a single detection/recording device 2. A pyramidal mirror 13 can join the images of multiple organoid chambers 20 into a single condensed viewpoint to maximize image resolution, while permitting the individual organoid chambers 20 to be spaced physically apart from each other.

Figure 9:
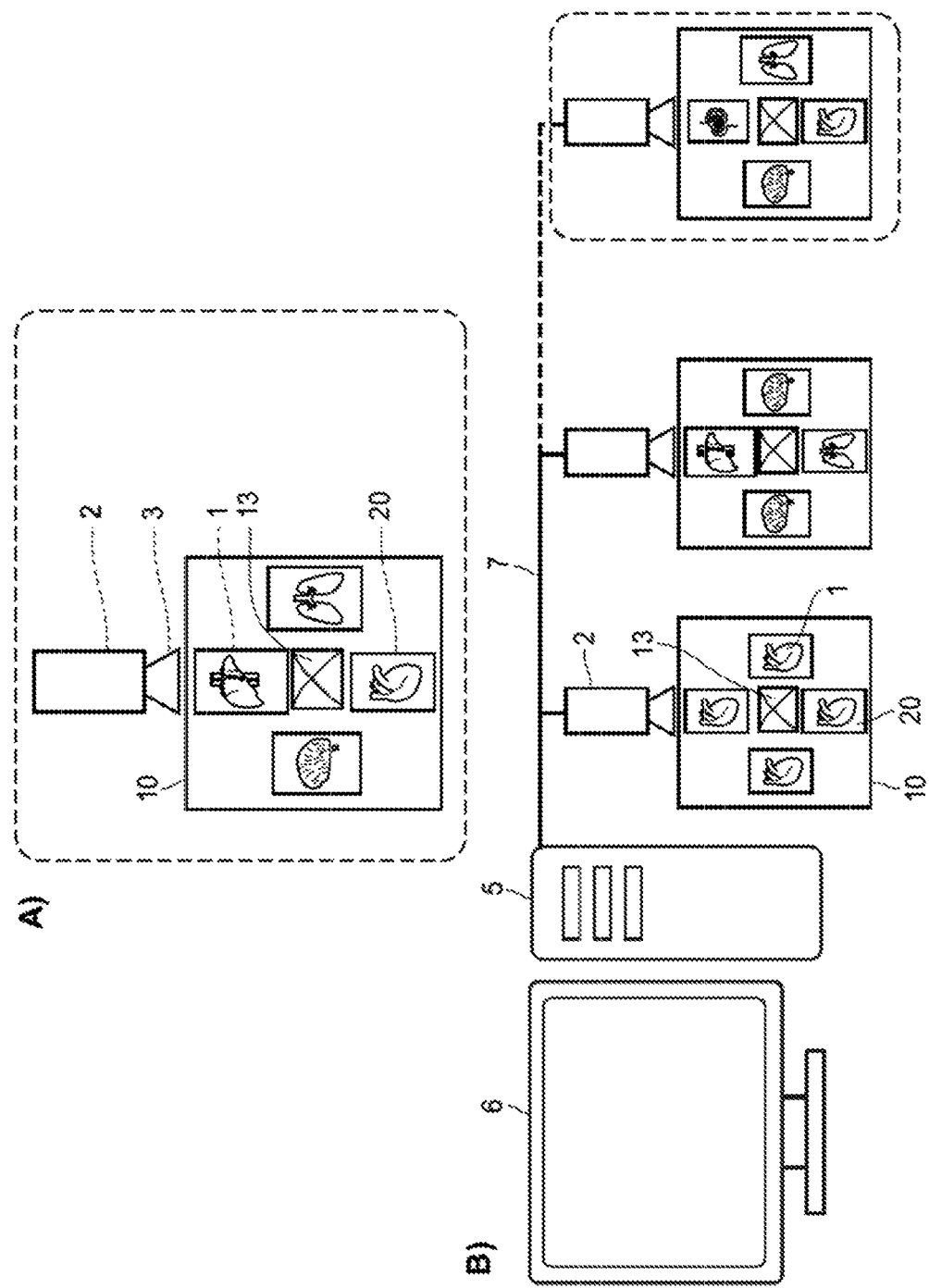
FIG. 9. A) A schematic illustration of a bioreactor system comprising an organoid module 10, a computer-controlled detection/recording device 2 (e.g., a camera) for simultaneously imaging up to four organoid cartridges 20 (and optionally saving the images), each containing an organoid 1 (e.g., heart, brain, nerve, liver, kidney, adrenal gland, stomach, pancreas, gall bladder, lung, small intestine, colon, bladder, prostate, uterus, blood, vascular, tumor, eye, or skin), via reflective pyramidal mirror 13. An organoid module 10 may contain a multiple of the same type of organoid 1 or a variety of organoid 1 types. B) A diagram of the imaging bioreactor platform consisting of a computer or data processor 5 controlling an array of organoid modules 10.

FIG. 9 illustrates elements of an embodiment of the bioreactor system that are involved in fluid movements, e.g., media flow, particularly the fluid movements involved in adding, or feeding, fresh media and removing, or aspirating, spent, or waste, media. FIG. 9A illustrates the entirety of the fluidic exchange system for a single organoid chamber 20 in organoid module 10, with FIG. 9B providing the combination of activated valves and pumps for aspiration and FIG. 9C providing the combination for feeding fresh media. The components of the system involved in fluid, e.g., media, movements can be located within, or without, organoid module 10. In describing an embodiment of the bioreactor system providing fluid movements as illustrated in FIG. 9, attention will be focused on FIG. 9B for media aspiration and on FIG. 9C for feeding of media to cells, tissues and organoids of the disclosure. It is understood that the combined descriptions of aspiration and feeding will provide a description of the complete fluid communications within an embodiment of the bioreactor system, as illustrated in FIG. 9A. In the remaining description of FIG. 9, attachments are to be understood as providing fluid communication between the attached components.

Turning now to the features of FIG. 9B involved in one embodiment of the bioreactor system for aspirating media, media 93 is in contact with chamber media-junction D tubing 86, which is attached to junction D valve 67. Also attached to junction D valve 67 is organoid-junction D tubing 85. In addition, junction D valve 67 is attached to junction D-pump C tubing 87, which is attached to pump C 72. Pump C 72 is attached to pump C-junction C tubing 88, which is attached to junction C valve 66. Junction C valve 66 is attached to junction C-mix/recycle tank tubing 89, which in turn is attached to mix/recycle tank 73. In some embodiments, media 93 is recycled and routed towards mix/recycle tank 73. Junction C valve 66 is also attached to junction C-waste tubing 90 leading from junction C valve 66 to waste.

In operation, the feeding of cells of the organoid, involves components highlighted in FIG. 9C, including fresh media tank 60, which is attached to fresh media-junction B tubing 78, which in turn is attached to junction B valve 65. Junction B valve 65 is attached to junction B-pump B tubing 79, which is attached to pump B 71. Pump B 71 is in turn attached to pump B-junction E tubing 80, which is attached to junction E valve 68. Junction E valve 68 is also attached to junction E-junction F tubing 82, which is attached to junction F valve 69. Also attached to junction F valve 69 is chamber media-junction F tubing 83, which also contacts chamber media 93.

Additional attached components are described that provide fluid communication within the system and permit additional functions including but not limited to, therapeutic additive dilution, perfusion of therapeutic(s), therapeutic washout of organoid, rinsing of fluidic lines, and the like. Fresh media tank 60 is attached to, and in fluid communication with, fresh media-junction A tubing 74, which in turn is attached to, and in fluid communication with, junction A valve 64, e.g., a three-way fluid controller or valve. Additive container 62, e.g., a therapeutic container, is used to deliver at least one therapeutic to additive tank 63, which is attached to additive tank-junction A tubing 75, which in turn is attached to junction A valve 64. Junction A valve 64 is also attached to junction A-pump A tubing 76, which is attached to pump A 70. Pump A 70 is attached to pump A-mix/recycle tank tubing 77, which is in turn attached to mix/recycle tank 73. In some embodiments, media from fresh media tank 60 is used to dilute therapeutic(s) from additive tank 63 within mix/recycle tank 73. Mix/recycle tank 73 is also attached to mix/recycle tank-junction B tubing 92, which in turn is attached to junction B valve 65. Junction E valve 68 is attached to junction E-organoid chamber tubing 81. In some embodiments, media can be delivered through junction E-organoid chamber tubing 81 to increase pressure within organoid 1. A pressure probe, i.e., pressure transducer 95, detects pressure, and changes in pressure, within an organoid 1 and converts the pressure to an analog electrical signal that is typically transmitted to the data processor, thereby allowing pressure to be monitored and adjusted by the system. In addition, the device provides for the washout or rinsing of fluidic lines. In particular, junction F valve 69 is attached to junction F-waste tubing 84, which in turn leads from junction F valve 69 to waste. In some embodiments, fluid can be removed from the fluid exchange system without coming in contact with organoid chamber 20 by exiting to waste through junction F-waste tubing 84.

Figure 10:
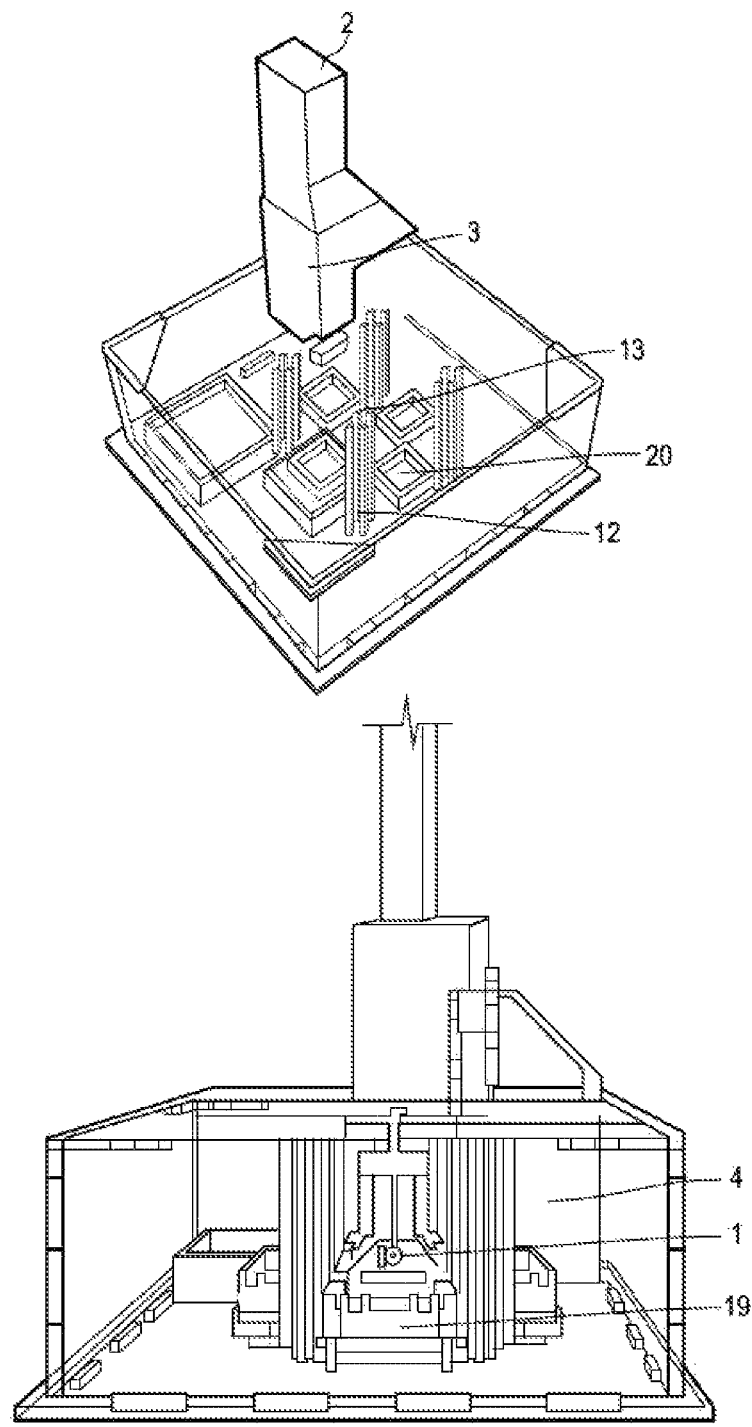
FIG. 10. Three-dimensional rendering of an organoid module 10 with four organoid cartridges 20. Isometric and side views are presented. Also shown is an organoid 1, a detection/recording device 2 connected to a lens 3, lights 12 (e.g., LED lights), a pyramidal mirror 13, an organoid cartridge 20, a temperature control element 4 (e.g., a heater), and a mixer 19, such as a stir bar.

FIG. 10 presents a higher-level schematic of fluidic exchange within organoid module 10 to illustrate the creation of a "body-in-a-jar". FIG. 10A presents a fluidic exchange system that transfers media between at least two organoid chambers 20 within organoid module 10. Fluid is directed through the system by a series of valves and pumps. FIG. 10B illustrates a fluidic exchange system where fluid is directed by valves and is pumped solely by a biological pump (e.g., a heart organoid 1), thereby providing a self-powered "body-in-a-jar".

Figure 11:
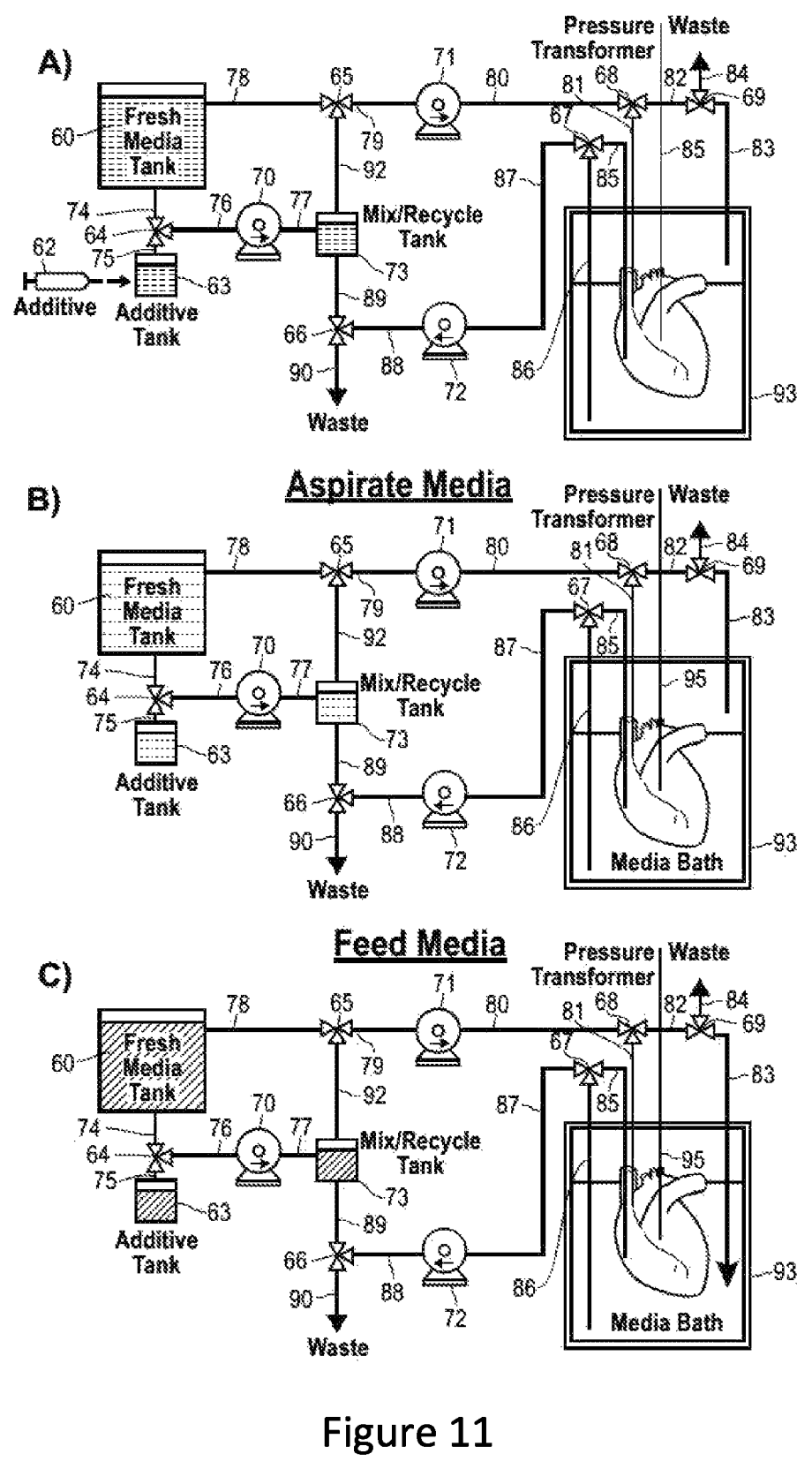

FIG. 11 presents methods of flowing fluid into and out of organoids 1. FIG. 11A illustrates an organoid 1 (left panel: heart organoid; right panel: liver organoid) connected to media inlet tube 26 and media outlet tube 28, which permits fluid to be directed into the void of the organoid 1 and out through media outlet tube 28 to a waste path. The direction of fluid flowing through the organoid 1 is controlled by inlet valve 27 and outlet valve 29. FIG. 11B represents a method of applying mechanical pressure to an organoid 1, such as a lung organoid 1. A fluidic pump controls fluid flow (e.g., gas or liquid) to organoid 1 and modulates the pressure of the organoid cavity to control the size of organoid 1. Absolute pressure values depend on the material properties of the organoid 1 and the desired size of the membrane for a given application. Applied relative pressures are adjusted for mechanical strain up to 25%.

As would be apparent to those in the field, some features of the bioreactor system are optional and most of the features of the system exist in a variety of embodiments. In some embodiments, cells can be sourced from any mammalian species or engineered as organoids 1 from cells and/or extracellular matrix. Any organ tissue type is suitable for use in the disclosed system, compositions and methods. For example, tissues can act as surrogates for any organ, including but not limited to the heart, brain, nerve, liver, kidney, adrenal gland, stomach, pancreas, gall bladder, lung, small intestine, colon, bladder, prostate, uterus, blood, vascular, tumor, eye, and skin.

Organoid chamber 20 containing organoid 1 is typically a cube made of a transparent solid that can be disposable or sterilizable, with at least two access ports such as doors. Suitable transparent solids include glass, and clear plastics such as polystyrene, acrylic and polycarbonate. Organoid chamber 20 can also be any polygonal shape provided that detection/recording device 2 can detect and record the behavior of cells in organoid 1 within organoid chamber 20. Given that the structure of organoid chamber 20 is limited by the need to allow detection/recording device 2 to detect cell behavior, it is apparent that a variety of transparent and translucent materials may be used in constructing organoid chamber 20. Even opaque materials are envisioned in embodiments where detection/recording device 2 is not detecting the transmission of visible light from organoid 1. Organoid chamber 20 is also constructed to be fluid-tight, thereby allowing organoid chamber 20 to contain chamber media 93 to feed the cells of organoid 1. Also, a chamber lid can provide apertures for penetration of at least one electrode or a pressure probe, i.e., pressure transducer 95.

At least one organoid chamber 20 is contained in an organoid module 10, which is formed from materials similar to the materials used for organoid chamber 20. Organoid modules 10 are typically square or rectangular in plane view, and typically contain a top in addition to a bottom. Organoid modules 10 are sized to accommodate at least 1, 2, 3, 4, 5, 6, 8, 10, or more organoid chambers 20. The walls, top and bottom of organoid module 10 are typically formed of a transparent solid such as glass or a clear plastic (e.g., acrylic or polycarbonate), but may also be formed of translucent or opaque materials provided that detection/recording device 2 can detect, and record, cell behavior. Organoid module 10 also typically contains one or more light sources 12, and one or more mirrors 13, such as a pyramidal mirror 13. In several embodiments, there is at least one light source 12 and at least one surface of a mirror 13 for each organoid chamber 20 contained in an organoid module 10.

Remaining components of the system include tanks, such as fresh media tank 60, mix/recycle tank 73, and additive tank 63, which are vessels for containing fluids used in the system. Such tanks can be any of a variety of dimensions and made from any of a number of materials, provided that the tanks as constructed can be used in an environment designed to minimize biological contamination, such as a sterile environment, and provided that the material used is compatible with the creation of one or more ports for fluid movement. Embodiments of the system may also involve one or more pumps, such as pump A 70, pump B 71 and pump C 72, and such pumps can be the same or different and can operate on any principle known to provide for the movement of fluids such as air and/or media through tubes. Exemplary pumps include peristaltic pumps, siphon pumps compatible with sterile environments, positive-displacement pumps such as piston-driven pumps, and non-positive-displacement pumps such as centrifugal pumps. In some embodiments, gravity is used to move fluids and no pumps are used to move, e.g., media.

Organoid module 10 also can interface with various tubes to move gas, such as air, used to provide pressure, e.g., inflate an organoid, which can be a balloon (e.g., a 6-Fr silicon Foley catheter balloon) or to move fluid. Pressure variations sufficient to control the inflation of a balloon or to move fluid in the system are achieved at pressures compatible with the use of a wide array of tube types and not just tubing certified to handle high pressure. For example, clear, plastic, flexible tubing is suitable for use, such as Tygon® tubing. Moreover, the various tubes can be combined into a single run of tubing as noted above, and such combined tubing is particularly well-suited for use with peristaltic pumps. Additionally, the tubing used in a given embodiment can vary in composition, internal diameter and external diameter. Another feature of the system are the junctions. Junctions typically are connected or attached to two or three tubes, which can vary in diameter and composition, as noted above. These junctions can be mere conduits or, more typically, are valves capable of directing the flow of fluid such as media from any attached tube to any other one or two attached tubes. Additional features and variations thereof will become apparent from the entirety of the disclosure provided herein.

In some embodiments, the organoid model has inflow and outflow fluid pathways (FIG. 11A). Valves (e.g., check valves, solenoid valves) control the direction of fluid movement in and out of an organoid with a cavity. In some embodiments, a single shaft or tube for inflow and outflow is contemplated (FIG. 11B). A fluidic pump controls fluid flow rate into and out of the organoid. In some embodiments, unequal inflow and outflow fluid rates are used to control the amount of fluid within the organoid. Adjusting the volume within the organoid cavity results in mechanical stretch in pliable organoids. In some embodiments, stretch is applied as a step function (passive stretch) or a sigmoidal function (cyclic stretch). Mechanical stretch is considered to be a mechanotransduction signal in many organoid types. In some embodiments, a combination of mechanical and electrical stimulation presents a more robust response for therapeutic screening.

A fluidic exchange system automates routine media changes, adjusts intraluminal pressure, perfuses therapeutics during screening, and exchanges media between organoids (FIGS. 10 and 11). The fluidic system consists of a series microfluidic pumps, 3-way valves controlled by a digital output board, and media reservoirs. Changing the valve configuration alters the direction in which media travels. In some embodiments, fluid can be added to, or removed from, a hollow vertical mounting shaft to which an organoid is connected, thus adjusting the hydrostatic pressure. A pressure transducer 95 and signal conditioner (e.g., OPP-M and LifeSens) senses the mean pressure within the organoid and communicates with the pumps via LabVIEW to adjust for a desired intraluminal pressure. Additionally, the fluidic exchange system is used for mixing and perfusion of therapeutics to the organoid. A solution is pumped from the additive tank and mixed with the circulating media. The therapeutic then perfuses into organoid chamber 20 and through organoid 1, similar to drug delivery via blood flow in humans. In some embodiments, the fluidic system of pumps and valves connects at least two organoid chambers 20 within an organoid module 10 to permit exchange of media and/or therapeutic(s) between or among the organoids 1. Additionally, in some embodiments the fluidic exchange system between organoid chambers 20 is powered by a biological pump in the form of an organoid 1, such as a cardiac organoid 1.

System Controls

Figure 12:
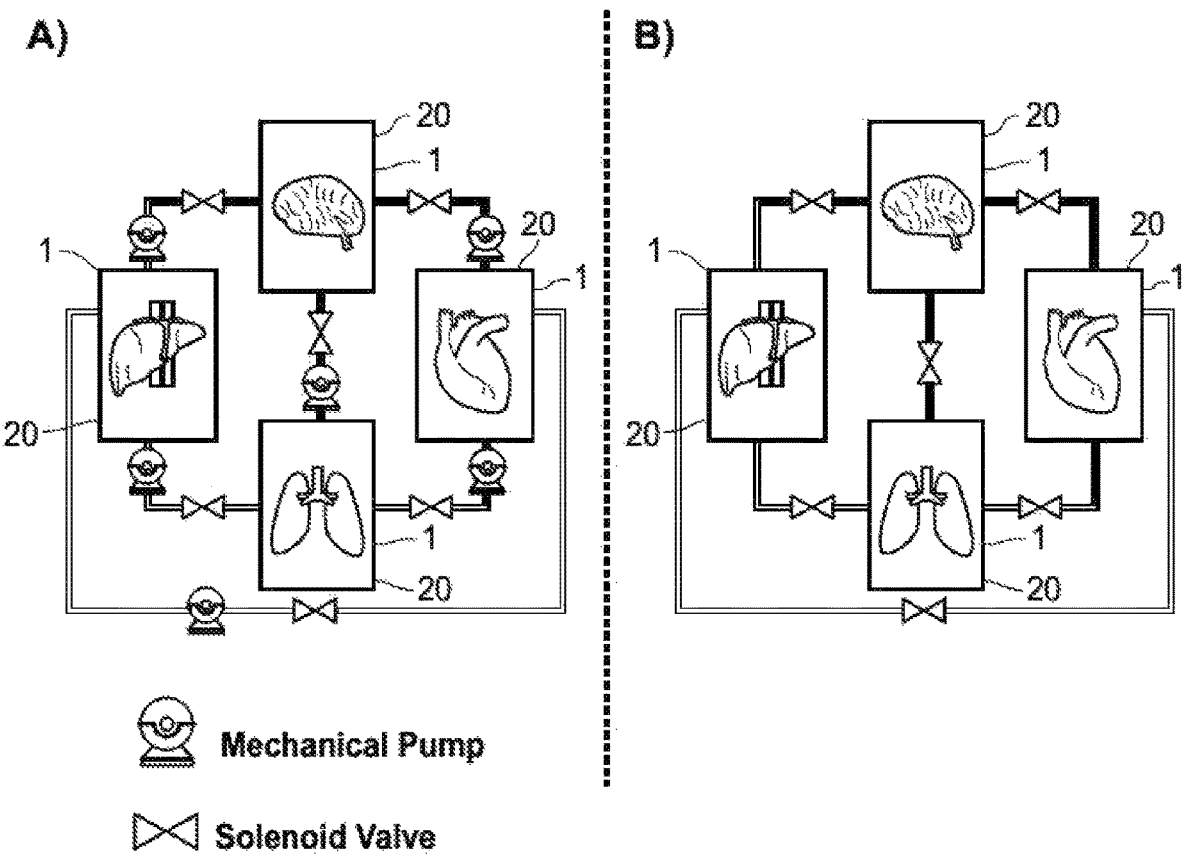
FIG. 12. A) Graphical representation of fluidic exchange system consisting of fluidic lines, pumps, and valves that direct media between multiple organoid cartridges within a module. A variety of organoid types can be connected to simulate a "body-in-a-jar". B) A heart organoid with sufficient pumping ability could be utilized as the sole biological pump to form a self-powered "body-in-a-jar". Example 1 provides additional description of these embodiments of the bioreactor system.
Figure 14:
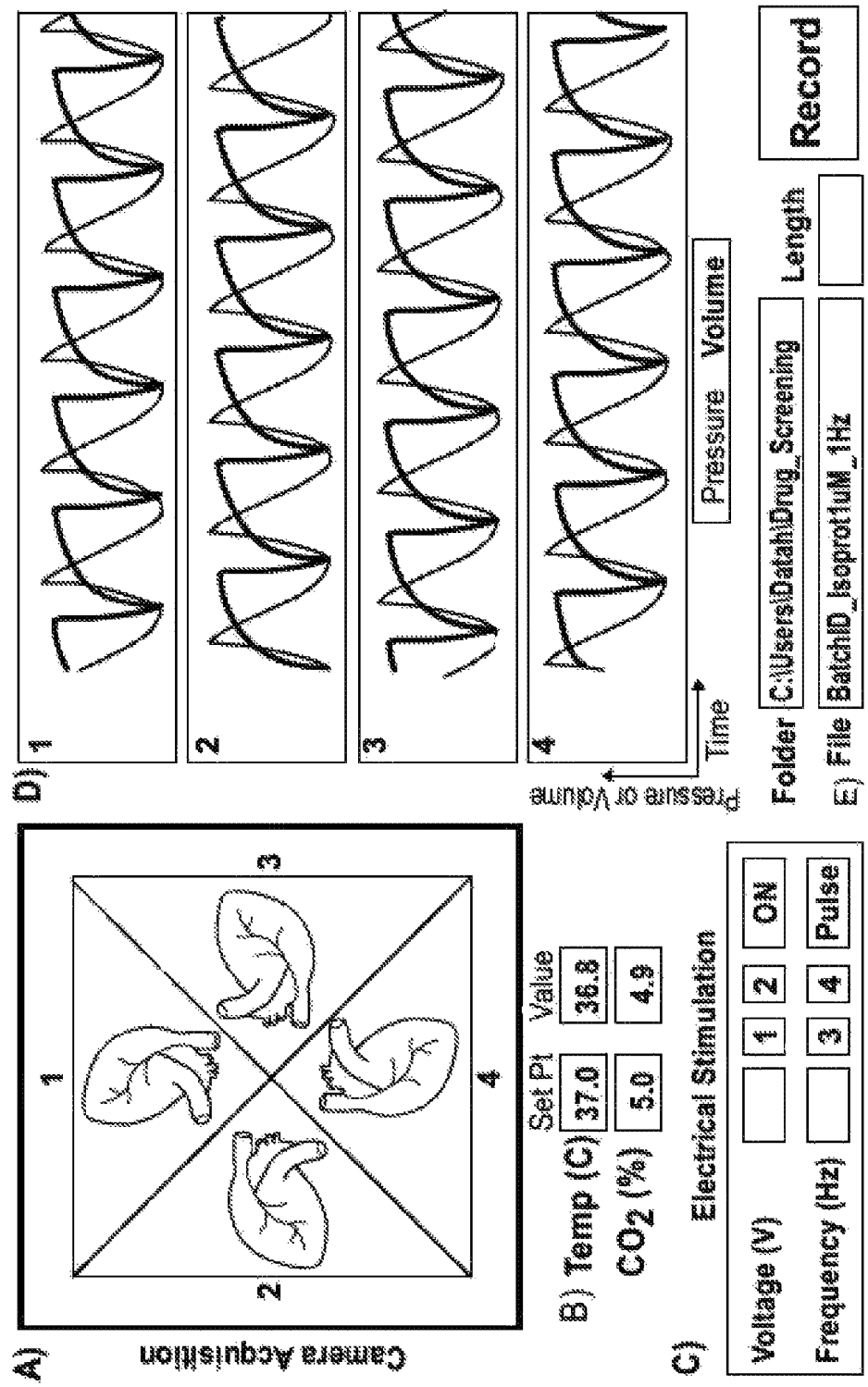
FIG. 14. Schematic of LabVIEW front panel for operating the bioreactor platform or system. A) Acquisition preview window of multiple organoids. B) Environmental control panel. C) Electrical stimulation parameters. The user has options to control the voltage power, alter the frequency, select which chambers to stimulate and decide to send continual stimulation or a single pulse. D) Real-time pressure, volume data of four distinct organoids. Pressure is represented as grey lines while organoid volume is represented as black lines. E) Recording parameters.
Figure 16A:
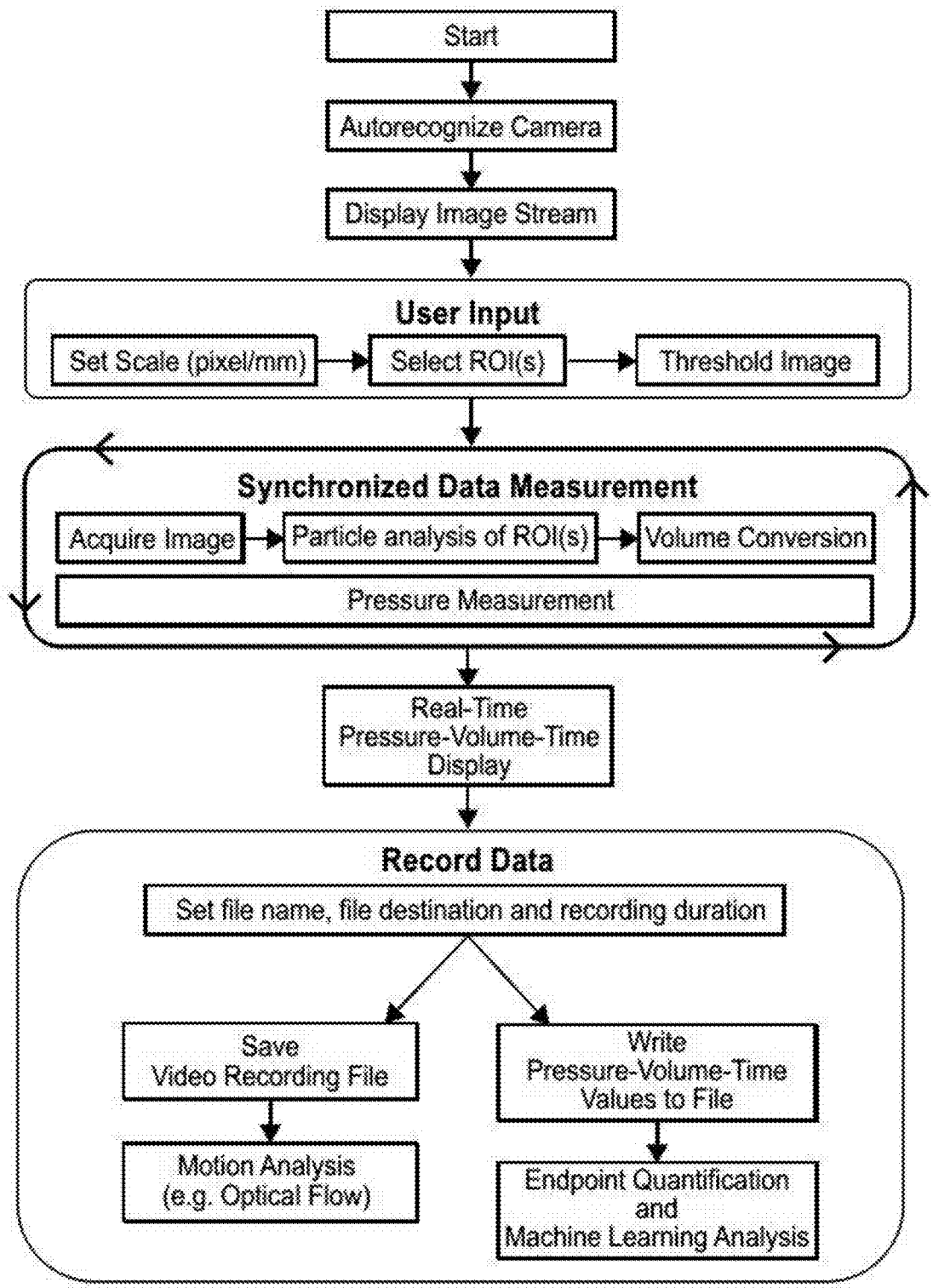
FIGS. 16A-16C. Flow diagrams of LabVIEW software used to monitor cells, tissues, and organoids in the system and apparatus disclosed herein. Flow diagrams schematically exemplify the software-based control of environmental variables, such as temperature and $CO_2$ level, and the software-based control of features of the system and apparatus, such as lens control, control of lighting, and control of electrical stimulation of cells, tissues and/or organoids contained in the system or apparatus.
Figure 16B:
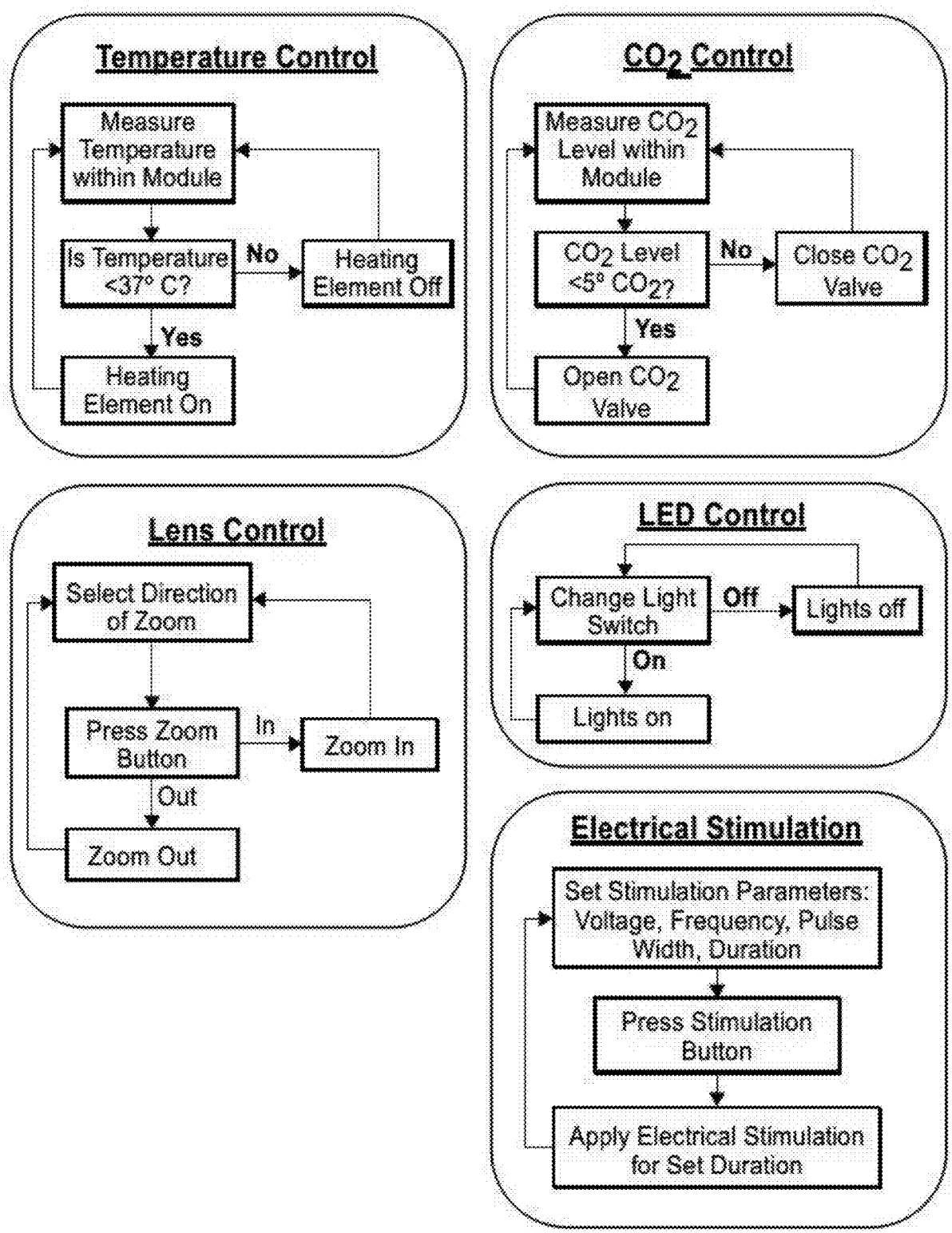
Figure 16C:
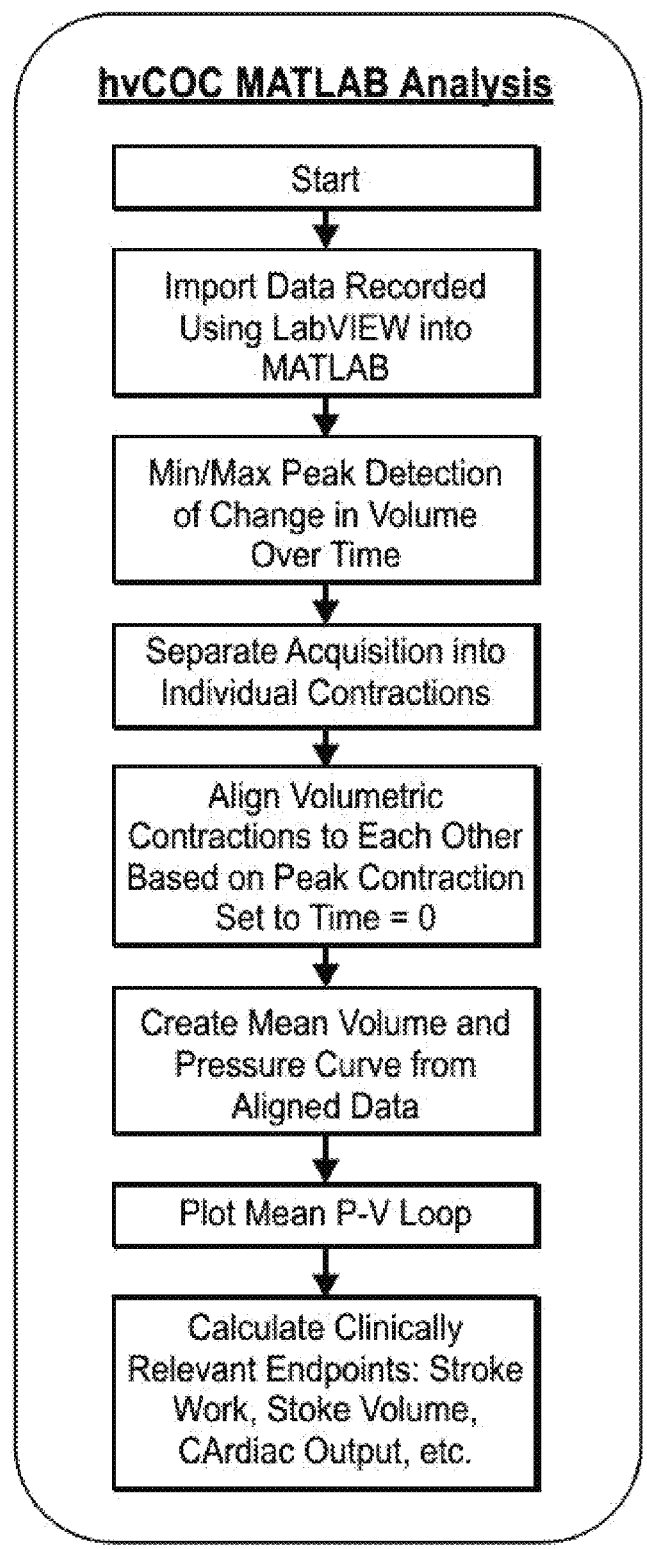

Custom LabVIEW code automates a large portion of the process, including both hardware and software. Each organoid module 10 is discretely controlled via a single LabVIEW-powered computer (i.e., data processor 5). See FIG. 14 for exemplary software flow diagrams. Therefore, multiple organoids 1 and multiple organoid modules 10 are, or can be, monitored simultaneously under different conditions (FIG. 12). The LabVIEW code controls relevant hardware, such as data acquisition devices, multichannel digital output sources, valves, pumps and camera capture cards. Therefore, the code electronically controls multiple functions of the bioreactor platform or system, such as automatic drug perfusion and mixing, intraluminal pressure control, electrical stimulation, $CO_2$ and temperature control, and pressure transduction with synchronized image capture. The computer is outfitted with enough memory and storage space to continually capture data (e.g., sufficient for at least 24 hours of continuous data collection). Image acquisition is synchronized with other acquisition modalities of the system (e.g., intra-organoid pressure measurements) to enable clinically relevant endpoint measurements (e.g., pressure-volume loops). Several analytical functions within the LabVIEW code enhance and simplify user functionality of the system. Particle analysis of threshold digital images quantifies real-time volume of multiple discrete organoids 1, e.g., via a pyramidal mirror 13, which can be used to calculate contractile characteristics in real time for relevant organoids 1. These functions are, or can be, combined with the control of an electrical stimulator for automatic maximum capturing frequency analysis and related electrophysiological testing protocols. For example, for heart organoids 1, the LabVIEW code begins by sending a 0.5 Hz biphasic electrical stimulation pulse to the heart organoid 1 and monitors whether the organoid 1 captures the current frequency. The code automatically increases the rate of electrical stimulation until 1:1 capture is lost, where the heart organoid 1 beating frequency ceases to match the stimulation rate. Recording date, drug intervention times, electrical pacing regimens and additional information on each organoid 1 probed are saved as metadata for archiving and quality control purposes.

Data Capture

Figure 13:
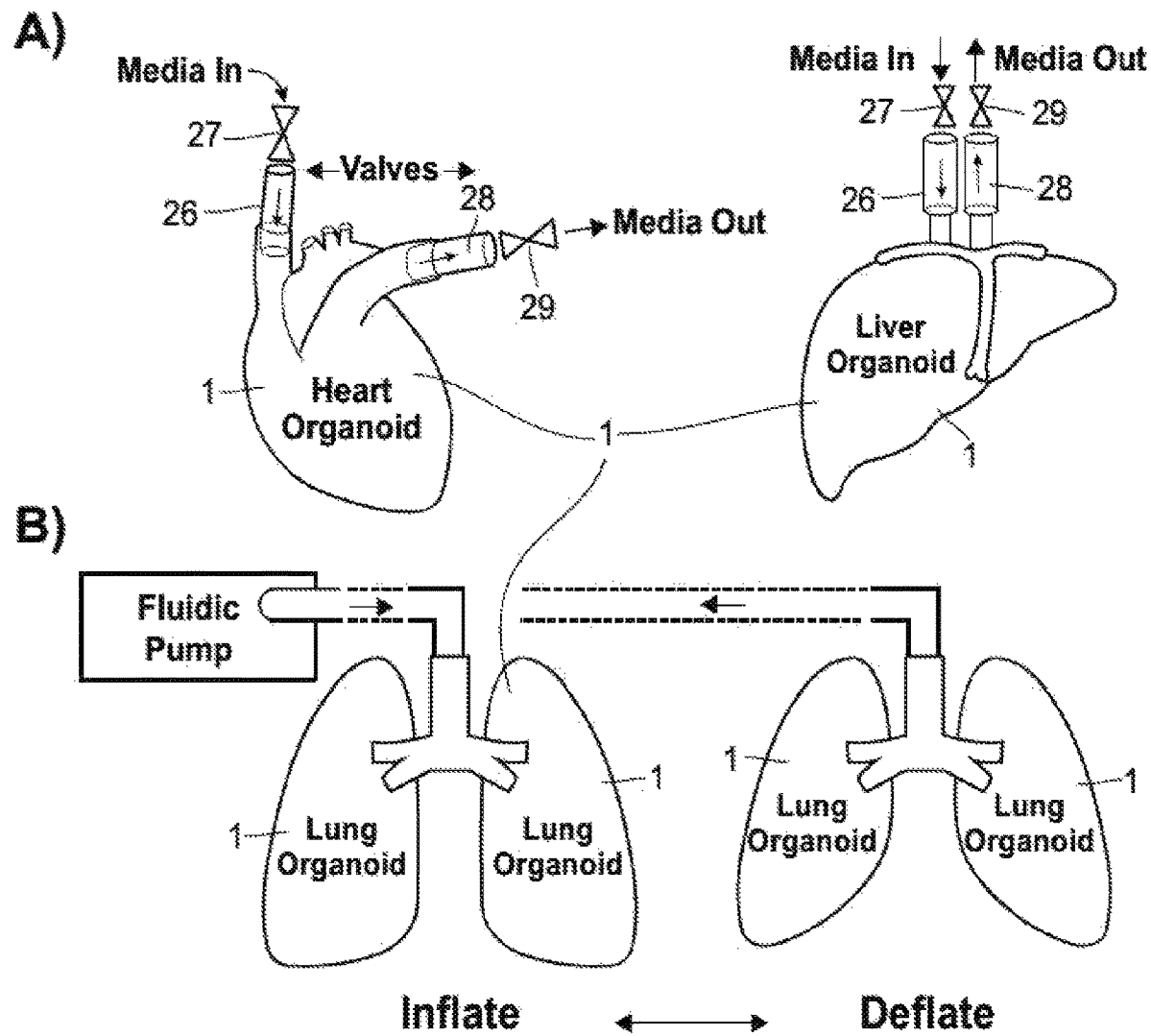
FIG. 13. A) An embodiment of the bioreactor system is illustrated that shows inlet and outlet pathways for media exchange through an organoid 1 controlled by valves (left pane: heart organoid; right pane: liver organoid). B) Schematic of mechanical stimulation system where a reversible fluidic pump is connected to an organoid 1 for inflation and deflation. The organoid 1 is subject to stretch based on changes in pressure delivered by the stimulation system and the pliability of the organoid 1.

Pressure and volume data are recorded simultaneously to generate pressure-volume curves in relevant contractile organoids. A high speed digital camera (Allied Vision) acquires images up to 100 frames/second. Organoid volume is estimated by assuming an equivalent sphere with the same cross-sectional area. A single acquisition typically contains multiple contractions. To characterize an organoid for its mean contraction characteristics, MATLAB code first separates the curve into discrete contractions. The data from each contraction are then aligned and averaged (FIG. 13A). The average pressure curve and average volume curve can then be plotted as the mean P-V loop (FIG. 13B).

Recorded high-speed brightfield videos are analyzed (e.g., optical flow) to characterize the motion pattern of the contractile organoids. Changes in contractile profile are analyzed to confirm therapeutic effects on organoid contractile performance. To handle the large amount of multidimensional data acquisition, machine learning algorithms determine key parameters that correlate with a therapeutic response and, ultimately, classify unknown therapeutics into categories of interest. Additionally, machine learning can be executed concurrently with long-term data acquisition to identify rare abnormal events and minimize data storage. For example, long-term data acquisition can be broken into a continuous series of acquisitions. Completed acquisitions are sent to the buffer to be analyzed as further acquisitions continue. Machine learning (e.g., binary support vector machine) evaluates any abnormality in function from data within the buffer, such as a rare abnormal event. If an abnormality is detected, then the relevant data are permanently stored, while normal function data are discarded.

Organoid Module

In some embodiments of the bioreactor system disclosed herein, the enclosure (about 25×25×15 cm) is made of a sterilizable material with a detection/recording device 2, e.g., a camera, and a temperature control element 4, e.g., a heating unit, attached to the roof of the organoid module 10. In some embodiments, the temperature control element 4, e.g., in the form of a heater, is placed within the enclosure. The vertical camera is focused onto a four-sided 45-degree pyramidal mirror 13 that reflects the side profile of one or multiple organoids 1 upwards to the camera. Angled LED lights 12 evenly illuminate the side profile of each organoid 1. Access doors allow interchangeable organoid chambers 20 to simply be inserted into the organoid module 10 for monitoring and then taken out for other experimental analyses (e.g., optical mapping). After therapeutic administration to the organoid 1, the media 93 is mixed using a mixer 19 in the form of a miniature magnetic stirrer (e.g., ThermoSci Micro Stirrer) that can be switched on and off using software control. Each organoid module 10 is temperature-controlled using a temperature control element 4 comprising a thermostat, heater and fan (e.g., IncuKit Mini). $CO_2$ levels are also individually controlled at 5% for cell culture buffering.

The platform's $CO_2$ control system comprises a single tank connected to a pressure regulator, routed to a solenoid valve manifold (e.g., Takasago CTV-2-4MIC) and finally a flowmeter (Dwyer Mini-Master Flowmeter) before connection to each organoid module 10. Each valve is individually controlled via a multichannel digital output module (e.g., NI-9472). A $CO_2$ sensor (e.g., SprintIR) within the enclosure measures the $CO_2$ level and controls the valve to switch between open and closed states. Additional sensors (e.g., $O_2$ sensor) are contemplated for incorporation to further control specific partial pressures within the enclosed environment.

Although the microfluidic connection of a variety of microtissues to form a "body-on-a-chip" has been pursued, a bioreactor platform for larger, macroscopic organoids to form a complex, interconnected "body" has not yet been described. Microtissues are not ideal for emulating human organ response as they lack key features of larger organs, such as the diffusion limitations of thicker tissues. A system that permits fluidic exchange between multiple macroscopic organoids recapitulates critical physiological and pharmacological features of the human body. The ability to measure multiple functional properties in a simplified biomimetic model of the human body provides new avenues to bridge the long-standing gap between traditional cell culture systems, in vivo animal models and clinical trials. In combination with somatic reprogramming of induced hPSC, the "human-body-in-a-jar" system is expected to serve as a versatile platform for next-generation drug discovery, cardiotoxicity screening, disease modeling and other ethnicity-, sex- and patient-specific applications.

REFERENCES

1. Martelli A, Puccio H. Dysregulation of cellular iron metabolism in Friedreich ataxia: From primary iron-sulfur cluster deficit to mitochondrial iron accumulation. Front Pharmacol. 2014; 5:130.
2. Dixon S J, Stockwell B R. The role of iron and reactive oxygen species in cell death. Nat Chem Biol. 2014; 10:9-17.
3. Kipps A, Alexander M, Colan S D, Gauvreau K, Smoot L, Crawford L, Darras B T, Blume E D. The longitudinal course of cardiomyopathy in Friedreich's ataxia during childhood. Pediatr Cardiol. 2009; 30:306-310.
4. Casazza F, Morpurgo M. The varying evolution of Friedreich's ataxia cardiomyopathy. Am J Cardiol. 1996; 77:895-898.
5. Lynch D R, Regner S R, Schadt K A, Friedman L S, Lin K Y, St John Sutton M G. Management and therapy for cardiomyopathy in Friedreich's ataxia. Expert Rev Cardiovasc Ther. 2012; 10:767-777.
6. Weidemann F, Liu D, Hu K, Florescu C, Niemann M, Herrmann S, Kramer B, Klebe S, Doppler K, Uceyler N, Ritter C O, Ertl G, Stork S. The cardiomyopathy in Friedreich's ataxia—new biomarker for staging cardiac involvement. Int J Cardiol. 2015; 194:50-57.
7. Tsou A Y, Paulsen E K, Lagedrost S J, Perlman S L, Mathews K D, Wilmot G R, Ravina B, Koeppen A H, Lynch D R. Mortality in Friedreich ataxia. J Neurol Sci. 2011; 307:46-49.
8. Rajagopalan B, Francis J M, Cooke F, Korlipara L V, Blamire A M, Schapira A H, Madan J, Neubauer S, Cooper J M. Analysis of the factors influencing the cardiac phenotype in Friedreich's ataxia. Mov Disord. 2010; 25:846-852.
9. Payne R M, Pride P M, Babbey C M. Cardiomyopathy of Friedreich's ataxia: Use of mouse models to understand human disease and guide therapeutic development. Pediatr Cardiol. 2011; 32:366-378.
10. Durr A, Cossee M, Agid Y, Campuzano V, Mignard C, Penet C, Mandel J L, Brice A, Koenig M. Clinical and genetic abnormalities in patients with Friedreich's ataxia. N Engl J Med. 1996; 335:1169-1175.
11. Filla A, De Michele G, Cavalcanti F, Pianese L, Monticelli A, Campanella G, Cocozza S. The relationship between trinucleotide (gaa) repeat length and clinical features in Friedreich ataxia. Am J Hum Genet. 1996; 59:554-560.
12. Isnard R, Kalotka H, Durr A, Cossee M, Schmitt M, Pousset F, Thomas D, Brice A, Koenig M, Komajda M. Correlation between left ventricular hypertrophy and gaa trinucleotide repeat length in Friedreich's ataxia. Circulation. 1997; 95:2247-2249.
13. Puccio H, Simon D, Cossee M, Criqui-Filipe P, Tiziano F, Melki J, Hindelang C, Matyas R, Rustin P, Koenig M. Mouse models for Friedreich ataxia exhibit cardiomyopathy, sensory nerve defect and fe-s enzyme deficiency followed by intramitochondrial iron deposits. Nat Genet. 2001; 27:181-186.
14. Al-Mandawi S, Pinto R M, Varshney D, Lawrence L, Lowrie M B, Hughes S, Webster Z, Blake J, Cooper J M, King R, Pook M A. Gaa repeat expansion mutation mouse models of Friedreich ataxia exhibit oxidative stress leading to progressive neuronal and cardiac pathology. Genomics. 2006; 88:580-590.
15. Miranda C J, Santos M M, Ohshima K, Smith J, Li L, Bunting M, Cossee M, Koenig M, Sequeiros J, Kaplan J, Pandolfo M. Frataxin knockin mouse. FEBS Lett. 2002; 512:291-297.
16. Hick A, Wattenhofer-Donze M, Chintawar S, Tropel P, Simard J P, Vaucamps N, Gall D, Lambot L, Andre C, Reutenauer L, Rai M, Teletin M, Messaddeq N, Schiffmann S N, Viville S, Pearson C E, Pandolfo M, Puccio H. Neurons and cardiomyocytes derived from induced pluripotent stem cells as a model for mitochondrial defects in Friedreich's ataxia. Dis Model Mech. 2013; 6:608-621.
17. Lee Y K, Ho P W, Schick R, Lau Y M, Lai W H, Zhou T, Li Y, Ng K M, Ho S L, Esteban M A, Binah O, Tse H F, Siu C W. Modeling of Friedreich ataxia-related iron overloading cardiomyopathy using patient-specific-induced pluripotent stem cells. Pflugers Arch. 2014; 466: 1831-1844.
18. Lee Y K, Lau Y M, Ng K M, Lai W H, Ho S L, Tse H F, Siu C W, Ho P W. Efficient attenuation of Friedreich's ataxia (frda) cardiomyopathy by modulation of iron homeostasis-human induced pluripotent stem cell (hipsc) as a drug screening platform for frda. Int J Cardiol. 2016; 203:964-971
19. Wang J, Chen A, Lieu D K, Karakikes I, Chen G, Keung W, Chan C W, Hajjar R J, Costa K D, Khine M, Li R A. Effect of engineered anisotropy on the susceptibility of human pluripotent stem cell-derived ventricular cardiomyocytes to arrhythmias. Biomaterials. 2013; 34:8878-8886.
20. Shum A M, Che H, Wong A O, Zhang C, Wu H, Chan C W, Costa K, Khine M, Kong C W, Li R A. A micropatterned human pluripotent stem cell-based ventricular cardiac anisotropic sheet for visualizing drug-induced arrhythmogenicity. Adv Mater. 2017; 29.
21. Chen A, Lieu D K, Freschauf L, Lew V, Sharma H, Wang J, Nguyen D, Karakikes I, Hajjar R J, Gopinathan A, Botvinick E, Fowles C C, Li R A, Khine M. Shrink-film configurable multiscale wrinkles for functional alignment of human embryonic stem cells and their cardiac derivatives. Adv. Mater. Weinheim 2011; 23:5785-5791.
22. Luna J, Ciriza J, Garcia-Ojeda M, Kong M, Herren A, Lieu D, Li R, Fowlkes C, Khine, M, McCloskey K. Multiscale Biomimetic Topography for the Alignment of Neonatal and Embryonic Stem Cell-Derived Heart Cells. Tissue Eng Part C Methods. 2011; 17:579-588.
23. Turnbull I C, Karakikes I, Serrao G W, Backeris P, Lee J-J J, Xie C, Senyei G, Gordon R E, Li R A, Akar F G, Hajjar R J, Hulot J-S, Costa K D. Advancing functional engineered cardiac tissues toward a preclinical model of human myocardium. FASEB J. 2014; 28:644-654.
24. Cashman T J, Josowitz R, Gelb B D, Li R A, Dubois N C, Costa K D. Construction of defined human engineered cardiac tissues to study mechanisms of cardiac cell therapy. J Vis Exp. 2016:e53447.
25. Weng Z, Kong C-W, Ren L, Karakikes I, Geng L, He J, Chow M Z, Mok C F, Keung W, Chow H, Leung A Y, Hajjar R J, Li R A, Chan C W. A simple, cost-effective but highly efficient system for deriving ventricular cardiomyocytes from human pluripotent stem cells. Stem Cells Dev. 2014; 23:1704-1716.
26. Goffart S, von Kleist-Retzow J C, Wiesner R J. Regulation of mitochondrial proliferation in the heart: Powerplant failure contributes to cardiac failure in hypertrophy. Cardiovasc Res. 2004; 64:198-207.
27. Ramirez R L, Becker A B, Mazurkiewicz J E, Feustel P J, Gelman B B, Koeppen A H. Pathology of intercalated discs in Friedreich cardiomyopathy. J Am Coll Cardiol. 2015; 66:1739-1740.
28. Edenharter O, Clement J, Schneuwly S, Navarro J A. Overexpression of *Drosophila* frataxin triggers cell death in an iron-dependent manner. J Neurogenet. 2017; 31:189-202.
29. Lopaschuk G D, Jaswal J S. Energy metabolic phenotype of the cardiomyocyte during development, differentiation, and postnatal maturation. J Cardiovasc Pharmacol. 2010; 56:130-140.
30. Keung, W., Ren, L., Sen Li, Wong, A. O., Chopra, A., Kong, C. W., Tomaselli G. F., Chen, C. S., Li, R. A. Non-cell autonomous cues for enhanced functionality of human embryonic stem cell-derived cardiomyocytes via maturation of sarcolemmal and mitochondrial K(ATP) channels. Sci Rep. 6, 34154 (2016).
31. Poon, E., Keung, W., Liang, Y., Ramalingam, R., Yan, B., Zhang, S., Chopra, A., Moore, J., Herren, A., Lieu, D. K., Wong, H. S., Weng, Z., Wong, O. T., Lam, Y. W., Tomaselli, G. F., Chen, C., Boheler, K. R. & Li, R. A. Proteomic Analysis of Human Pluripotent Stem Cell-Derived, Fetal, and Adult Ventricular Cardiomyocytes Reveals Pathways Crucial for Cardiac Metabolism and Maturation. Circ Cardiovasc Genet 8, 427-436 (2015).
32. Zhang, S., Poon, E., Xie, D., Boheler, K. R., Li, R. A., Wong, H. S. Consensus comparative analysis of human embryonic stem cell-derived cardiomyocytes. PLoS One. 10, e0125442 (2015).
33. Karakikes I., Stillitano F., Nonnenmacher M., Tzimas C., Sanoudou D., Termglinchan V., Kong C. W., Rushing S., Hansen J., Ceholski D., Kolokathis F., Kremastinos D., Katoulis A., Ren L., Cohen N., Gho J. M., Tsiapras D., Vink A., Wu J. C., Asselbergs F. W., Li R. A., Hulot J. S., Kranias E. G., Hajjar R. J. Correction of human phospholamban R14del mutation associated with cardiomyopathy using targeted nucleases and combination therapy. Nat Commun. 6, 6955 (2015).
34. Chen, G., Li, S., Karakikes, I., Ren, L., Chow, M. Z., Chopra, A., Keung, W., Yan, B., Chan, C. W., Costa, K. D., Kong, C. W., Hajjar, R. J., Chen, C. S., Li, R. A. Phospholamban as a crucial determinant of the inotropic response of human pluripotent stem cell-derived ventricular cardiomyocytes and engineered 3-dimensional tissue constructs. Circ Arrthyhm Electrophysiol. 8, 193-201 (2015).
35. Weng, Z., Kong, C.-W., Ren, L., Karakikes, I., Geng, L., He, J., Chow, M. Z. Y., Mok, C. F., Chan, H. Y. S., Webb, S. E., Keung, W., Chow, H., Miller, A. L., Leung, A. Y. H., Hajjar, R. J., Li, R. A. & Chan, C. W. A Simple, Cost-Effective but Highly Efficient System for Deriving Ventricular Cardiomyocytes from Human Pluripotent Stem Cells. Stem Cells Dev. 23, 1704-1716 (2014).
36. Karakikes, I., Senyel, G. D., Hansen, J., Kong, C.-W., Azeloglu, E. U., Stillitano, F., Lieu, D. K., Wang, J., Ren, L., Hulot, J.-S., Iyengar, R., Li, R. A. & Hajjar, R. j. Small Molecule-Mediated Directed Differentiation of Human Embryonic Stem Cells Toward Ventricular Cardiomyocytes. Stem Cells Transl. Med. 3, 18-31 (2014).
37. Li, S., Cheng, H., Tomaselli, G. F., Li, R. A. Mechanistic basis of excitation-contraction coupling in human pluripotent stem cell-derived ventricular cardiomyocytes revealed by Ca2+ spark characteristics: direct evidence of functional Ca2+-induced Ca2+ release. Heart Rhythm. 11, 133-140 (2014).
38. Poon, E., Yan, B., Zhang, S., Rushing, S., Keung, W., Ren, L., Lieu, D. K., Geng, L., Kong, C. W., Wang, J., Wong H. S., Boheler, K. R., Li, R. A. Transcriptome-guided functional analyses reveal novel biological properties and regulatory hierarchy of human embryonic stem cell-derived ventricular cardiomyocytes crucial for maturation. PLoS One. 8, e77784 (2013).
39. Chow, M. Z., Geng, L., Kong, C. W., Keung, W., Fung, J. C., Boheler, K. R., Li, R. A. Epigenetic regulation of the electrophysiological phenotype of human embryonic stem cell-derived ventricular cardiomyocytes: insights for driven maturation and hypertrophic growth. Stem Cells Dev. 22, 2678-2690 (2013).
40. Lieu, D. K., Fu, J. D., Chiamvimonvat, N., Tung, K. C., McNerney, G. P., Huser, T., Keller, G., Kong, C. W., Li, R. A. Mechanism-based facilitated maturation of human pluripotent stem cell-derived cardiomyocytes. Circ Arrhythm Electrophysiol. 6, 191-201 (2013).
41. Fu, J. D., Rushing, S. N., Lieu, D. K., Chan, C. W., Kong, C. W., Geng, L., Wilson, K. D., Chiamvimonvat, N., Boheler, K. R., Wu, J. C., Keller, G., Hajjar, R. J., Li, R. A. Distinct roles of microRNA-1 and -499 in ventricular specification and functional maturation of human embryonic stem cell-derived cardiomyocytes. PLoS One. 6, e27417 (2011).
42. Wilson, K. D., Hu, S., Venkatasubrahmanyam, S., Fu, J. D., Sun, N., Abilez, O. J., Baugh, J. J., Jia, F., Ghosh, Z., Li, R. A., Butte, A. J., Wu, J. C. Dynamic microRNA expression programs during cardiac differentiation of human embryonic stem cells: role for miR-499. Circ Cardiovasc Genet. 3, 426-435 (2010).
43. Fu, J. D., Jiang, P., Rushing, S., Liu, J., Chiamvimonvat, N., Li, R. A. Na+/Ca2+ exchanger is a determinant of excitation-contraction coupling in human embryonic stem cell-derived ventricular cardiomyocytes. Stem Cells Dev. 19, 773-782 (2010).
44. Liu, J., Lieu, D. K., Siu, C. W., Fu, J. D., Tse, H. F., Li, R. A. Facilitated maturation of Ca2+ handling properties of human embryonic stem cell-derived cardiomyocytes by calsequestrin expression. Am J Physiol Cell Physiol. 297, C152-159 (2009).

45. Lieu, D. K., Liu, J., Siu, C. W., McNerney, G. P., Tse, H. F., Abu-Khalil, A., Huser, T., Li, R. A. Absence of transverse tubules contributes to non-uniform Ca(2+) wavefronts in mouse and human embryonic stem cell-derived cardiomyocytes. Stem Cells Dev. 18, 1493-1500 (2009).
46. Chan, J. W., Lieu, D. K., Huser, T., Li, R. A. Label-free separation of human embryonic stem cells and their cardiac derivatives using Raman spectroscopy. Anal Cham. 81, 1324-1331 (2009).
47. Liu J., Fu J. D., Siu C. W., Li R. A. Functional sarcoplasmic reticulum for calcium handling of human embryonic stem cell-derived cardiomyocytes: insights for driven maturation. Stem Cells. 12, 3038-44 (2007).
48. Wang K., Xue T., Tsang S. Y., Van Huizen R., Wong C. W., Lai K. W., Ye Z., Cheng L., Au K. W., Zhang J., Li G. R., Lau C. P., Tse H. F., Li R. A. Electrophysiological properties of pluripotent human and mouse embryonic stem cells. Stem Cells. 10, 1526-34 (2005)
49. Li, R. A., et al., Bioengineering an electro-mechanically functional miniature ventricular heart chamber from human pluripotent stem cells. Biomaterials, 2018. 163: p. 116-127.
50. Weng, Z., et al., A simple, cost-effective but highly efficient system for deriving ventricular cardiomyocytes from human pluripotent stem cells. Stem Cells Dev, 2014. 23(14): p. 1704-16.

Each of the references cited herein is hereby incorporated by reference in its entirety or in relevant part, as would be apparent from the context of the citation.

It is to be understood that while the claimed subject matter has been described in conjunction with the detailed description thereof, the foregoing description is intended to illustrate and not limit the scope of that claimed subject matter, which is defined by the scope of the appended claims. Other aspects, advantages, and modifications are within the scope of the following claims.

What is claimed is:

1. A method for assaying a response of a cardiac organoid to a compound comprising:
   (a) preloading a cardiac organoid in at least one organoid module by adjusting a hydrostatic pressure inside an organoid chamber to induce a change in stroke work of between 1-50% normalized to an untreated baseline to expand the cardiac organoid prior to administering a compound, wherein the cardiac organoid is housed in at least one organoid module, each organoid module comprising:
      (i) a media inlet, a media outlet, and at least one wall compatible with an external detection device, wherein the cardiac organoid comprises at least one human cell, wherein the one human cell is a human embryonic stem cell, a human adult stem cell, a human induced pluripotent stem cell, a cell derived from a human tissue, or a progenitor cell of a human tissue, and wherein the cardiac organoid is in fluid communication with a fluid pump or a fluid reservoir comprising an adjustable volume of fluid, wherein the fluid pump or fluid reservoir modulates the pressure within the organoid;
      (ii) a mirror arrangement for simultaneous monitoring of any biological development of the cardiac organoid in each of at least two organoid chambers; and
      (iii) a detection device for observing the monitored biological development of the cardiac organoid in each of at least two organoid chambers;
   (b) administering the compound to the cardiac organoid; and
   (c) detecting a response of the cardiac organoid to the compound.
2. The method of claim 1 wherein the response is a positive inotropic response or a negative inotropic response.
3. The method of claim 1 wherein the compound is a pharmacological agent and the response is a response to the pharmacological agent.
4. The method of claim 1 wherein the compound is a known therapeutic.
5. The method of claim 4 wherein the known therapeutic is useful in treating a cardiac disease or disorder.
6. The method of claim 5 wherein the cardiac disease or disorder is dilated cardiomyopathy, hypertrophic cardiomyopathy, pulmonary atresia, Tetralogy of Fallot, dilated cardiomyopathy with ataxia or heterotaxy syndrome.
7. The method of claim 4 wherein the known therapeutic is useful in treating a non-cardiac disease or disorder having at least one cardiac effect.
8. The method of claim 7 wherein the non-cardiac disease or disorder is Friedreich's ataxia (FRDA), Kearns-Sayre syndrome, carbohydrate-deficient glycoprotein syndrome type Ia (phosphomannomutase-2 congenital defect of glycosylation Ia or PMM2-CDG-Ia), spinocerebellar ataxia, Wilson disease, Dandy-Walker syndrome, Leigh disease, mitochondria! encephalomyopathy, lactic acidosis, and stroke-like episodes (MELAS), or myoclonic epilepsy with ragged red fibers (MERRF).
9. The method of claim 1 wherein the compound is a candidate therapeutic for a cardiac disease or disorder, or for a non-cardiac disease or disorder.
10. The method of claim 1 wherein the change in stroke work is between 20-30% prior to administering the compound.
11. The method of claim 1 wherein the cardiac organoid is a healthy cardiac organoid, the method further comprising a comparison of the effect of the compound on the healthy cardiac organoid to the effect of the compound on a diseased cardiac organoid to reveal at least one phenotypic difference between the healthy and diseased cardiac organoids.
12. The method of claim 11 wherein the pressure applied to the healthy cardiac organoid and the diseased cardiac organoid is the same.
13. The method of claim 11 wherein the phenotypic difference is a difference in contractile force, contractile rate, or relaxation rate.
14. The method of claim 11 wherein the diseased cardiac organoid exhibits a developed pressure of less than 2 mm $H_2O$.
15. The method of claim 13 wherein the diseased cardiac organoid is from a subject with Friedrich's Ataxia.
16. The method of claim 1 wherein the cardiac organoid is electrically paced using 5 volts/cm at a frequency of 1.5 Hz.
17. The method of claim 1 wherein the stroke work is greater in the presence of the compound than in its absence, at a positive preloading of the cardiac organoid of at least 2.5 mm $H_2O$.
18. The method of claim 17 wherein the difference in stroke work increases as the degree of preloading increases from 2.5 mm $H_2O$ to 7.5 mm $H_2O$.
19. The method of claim 1 wherein the stroke work is lower in the presence of the compound than in its absence at a positive preloading pressure of the cardiac organoid of at least 2.5 mm $H_2O$.

20. The method of claim 19 wherein the difference in stroke work increases as the degree of preloading increases from 2.5 mm $H_2O$ to 7.5 mm $H_2O$.

21. The method of claim 1 wherein the organoid module further comprises a cartridge.

22. The method of claim 1, wherein the organoid module further comprises four cartridges.

* * * * *

UNITED STATES PATENT AND TRADEMARK OFFICE
CERTIFICATE OF CORRECTION

Page 1 of 1

PATENT NO. : 12,282,013 B2
APPLICATION NO. : 17/254264
DATED : April 22, 2025
INVENTOR(S) : Ronald A. Li et al.

It is certified that error appears in the above-identified patent and that said Letters Patent is hereby corrected as shown below:

On the Title Page

At item (87), Line 1, "WO2019/044044" should be -- WO2019/244044 --.

In the Claims

At Column 28, Line 28, "mitochondria!" should be -- mitochondrial --.

Signed and Sealed this
Ninth Day of December, 2025

John A. Squires
*Director of the United States Patent and Trademark Office*